United States Patent
Gafford et al.

(10) Patent No.: US 11,419,693 B2
(45) Date of Patent: Aug. 23, 2022

(54) POP-UP LAMINATE STRUCTURES WITH INTEGRATED ELECTRONICS

(71) Applicant: President and Fellows of Harvard College, Cambridge, MA (US)

(72) Inventors: Joshua B. Gafford, Somerville, MA (US); Samuel B. Kesner, Arlington, MA (US); Conor J. Walsh, Cambridge, MA (US); Michael Karpelson, Newton, MA (US); Robert J. Wood, Cambridge, MA (US); Zivthan Dubrovsky, Lexington, MA (US); Benjamin I. Goldberg, Boston, MA (US); Kathleen O'Donnell, Cambridge, MA (US); Michael J. Smith, North Reading, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 255 days.

(21) Appl. No.: 16/526,411

(22) Filed: Jul. 30, 2019

(65) Prior Publication Data

US 2020/0015920 A1 Jan. 16, 2020

Related U.S. Application Data

(63) Continuation of application No. 14/909,792, filed as application No. PCT/US2014/049588 on Aug. 4, 2014, now Pat. No. 10,376,326.

(Continued)

(51) Int. Cl.
*A61B 34/00* (2016.01)
*B81C 99/00* (2010.01)
(Continued)

(52) U.S. Cl.
CPC .......... *A61B 34/72* (2016.02); *A61B 18/148* (2013.01); *A61B 18/1442* (2013.01);
(Continued)

(58) Field of Classification Search
CPC .............. A61B 18/1442; A61B 18/148; A61B 2017/00039; A61B 2017/0011;
(Continued)

(56) References Cited

U.S. PATENT DOCUMENTS

| | | | |
|---|---|---|---|
| 6,593,841 B1 | 7/2003 | Mizoguchi et al. | |
| 2008/0214967 A1* | 9/2008 | Aranyi | A61B 17/320068 601/3 |

(Continued)

OTHER PUBLICATIONS

Felton et al, "Robot Self-Assembly by Folding: A Printed Inchworm Robot", IDDD Int'l Conf. on Robotics and Automation, pp. 277-282 (Year: 2013).*

(Continued)

*Primary Examiner* — Michael F Peffley
(74) *Attorney, Agent, or Firm* — Modern Times Legal; Robert J. Sayre

(57) ABSTRACT

A multi-layer, super-planar laminate structure can be formed from distinctly patterned layers. The layers in the structure can include at least one rigid layer and at least one flexible layer; the rigid layer includes a plurality of rigid segments, and the flexible layer can extend between the rigid segments to serve as a joint. The layers are then stacked and bonded at selected locations to form a laminate structure with inter-layer bonds, and the laminate structure is flexed at the flexible layer between rigid segments to produce an expanded three-dimensional structure, wherein the layers are joined at the selected bonding locations and separated at other locations. A layer with electrical wiring can be (Continued)

included in the structure for delivering electric current to devices on or in the laminate structure.

12 Claims, 24 Drawing Sheets

Related U.S. Application Data

(60) Provisional application No. 61/862,066, filed on Aug. 4, 2013.

(51) Int. Cl.

| | | |
|---|---|---|
| *A61B 18/14* | (2006.01) | |
| *B81B 7/00* | (2006.01) | |
| *H05K 1/02* | (2006.01) | |
| *H05K 1/18* | (2006.01) | |
| *A61B 17/00* | (2006.01) | |
| *A61B 17/29* | (2006.01) | |
| *A61B 90/00* | (2016.01) | |
| *A61B 18/00* | (2006.01) | |

(52) U.S. Cl.
CPC .......... *B81B 7/008* (2013.01); *B81C 99/0095* (2013.01); *H05K 1/0278* (2013.01); *H05K 1/18* (2013.01); *A61B 2017/0011* (2013.01); *A61B 2017/00039* (2013.01); *A61B 2017/00203* (2013.01); *A61B 2017/00345* (2013.01); *A61B 2017/00402* (2013.01); *A61B 2017/00526* (2013.01); *A61B 2017/00867* (2013.01); *A61B 2017/2926* (2013.01); *A61B 2018/00577* (2013.01); *A61B 2018/00595* (2013.01); *A61B 2018/146* (2013.01); *A61B 2090/064* (2016.02); *A61B 2562/028* (2013.01); *A61B 2562/0261* (2013.01); *B81B 2207/99* (2013.01)

(58) Field of Classification Search
CPC ........... A61B 2017/00203; A61B 2017/00345; A61B 2017/00402; A61B 2017/00526; A61B 2017/00867; A61B 2017/2926; A61B 2018/00577; A61B 2018/00595; A61B 2018/146; A61B 2090/064; A61B 2562/0261; A61B 2562/028; A61B 34/72; B81B 2207/99; B81B 7/008; B81C 99/0095; H05K 1/0278; H05K 1/18
See application file for complete search history.

(56) References Cited

U.S. PATENT DOCUMENTS

| | | |
|---|---|---|
| 2008/0257488 A1 | 10/2008 | Yamano |
| 2009/0105703 A1* | 4/2009 | Shadduck .......... A61B 18/1815 606/27 |
| 2010/0052082 A1 | 3/2010 | Lee et al. |
| 2010/0171881 A1 | 7/2010 | Manoukian et al. |

OTHER PUBLICATIONS

Grujicic et al, "Optimization of a piezoelectric bimorph grasper for use in minimally invasive surgical applications", Proc. IMechE vol. 219, pp. 1-11 (Year: 2005).*
Sterman, "PCB Origami: Folding ciruit boards into electronic products", (thesis) MIT (Year: 2013).*
Hawkes et al., "Programmable matter by folding", PNAS, vol. 107, No. 28, pp. 12441-12335 (Year: 2010).*
Agilent Technologies, "Practical Strain Gage Measurements", (catalog), pp. E94-E130 (Year: 2006).*
Menciassi et al, "Force Feeback-Based Microinstrument for Measuring Tissue Properties and Pulse in Microsurgery", IEEE Int. Conf Robotics and Automation, pp. 626-631 (Year: 2001).*
Baisch, "Design, Manufacturing, and Locomotion Studies of Ambulatory Micro-Robots", (thesis), Harvard Univesity, pp. 16-36 (Year: 2013).*
USPTO, International Search Report and Written Opinion for PCT/US14/49588 (dated Jan. 7, 2015).
S. Felton, et al., "Robot Self-Assembly by Folding: A Printed Inchworm Robot," 2013 IEEE Int'l Conf. on Robotics and Automation (ICRA), Karlsruhe, Germany, May 6-10, 2013, 277-282 (May 2013).
M. Grujicic, et al., "Optimization of a piezoelectric bimorph grasper for use in minimally invasive surgical applications," Proc. IMechE, vol. 219, Part B: J. Engineering Manufacture (Jun. 10, 2005).
Y. Sterman, "PCB Origami: Folding circuit boards into electronic products" (thesis) Massachusetts Institute of Technology (Jul. 19, 2013).
E. Hawkes, et al., "Programmable matter by folding", PNAS, vol. 107, No. 28, Programmable matter by folding, PNAS, Jul. 13, 2010, vol. 107, No. 28, 12441-12445 (Jul. 13, 2010).
Agilent Technologies, "Practical Strain Gage Measurements" (catalog) (Oct. 15, 2006).
A. Menciassi, et al., "Force feedback-based microinstrument for measuring tissue properties and pulse in microsurgery", (proceeding) Proc. IEEE Int. Conf. Robotics & Automation, Seoul, Korea, May 21-26, 2001 (May 2001).
A. Baisch, "Design, Manufacturing, and Locomotion Studies of Ambulatory Micro-Robots," (thesis) (Apr. 2013).

* cited by examiner

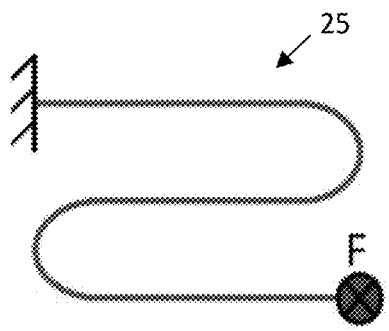
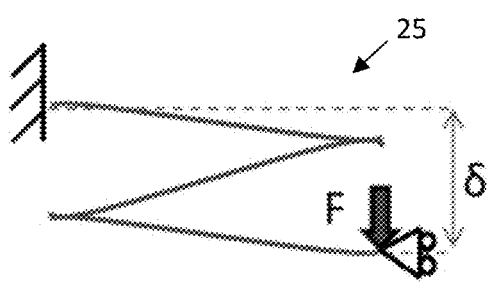
FIG. 8   FIG. 9
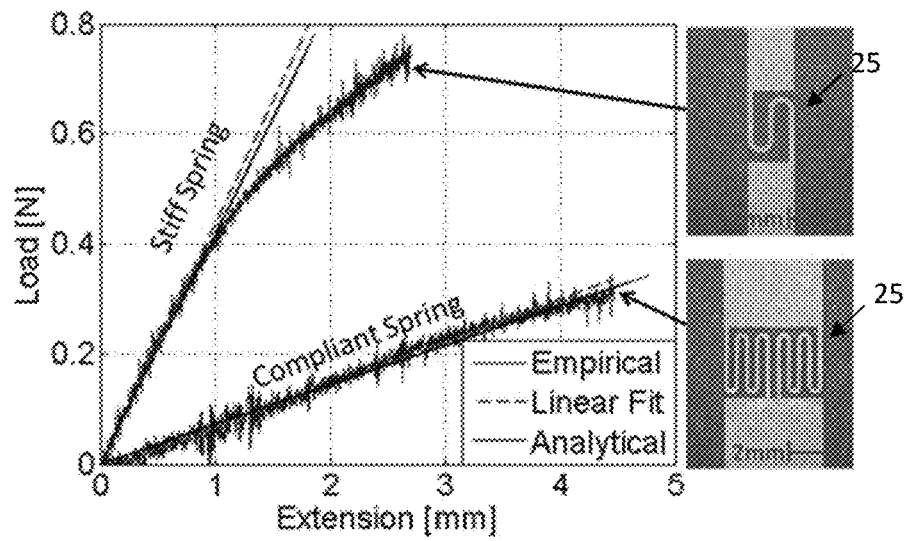
FIG. 10
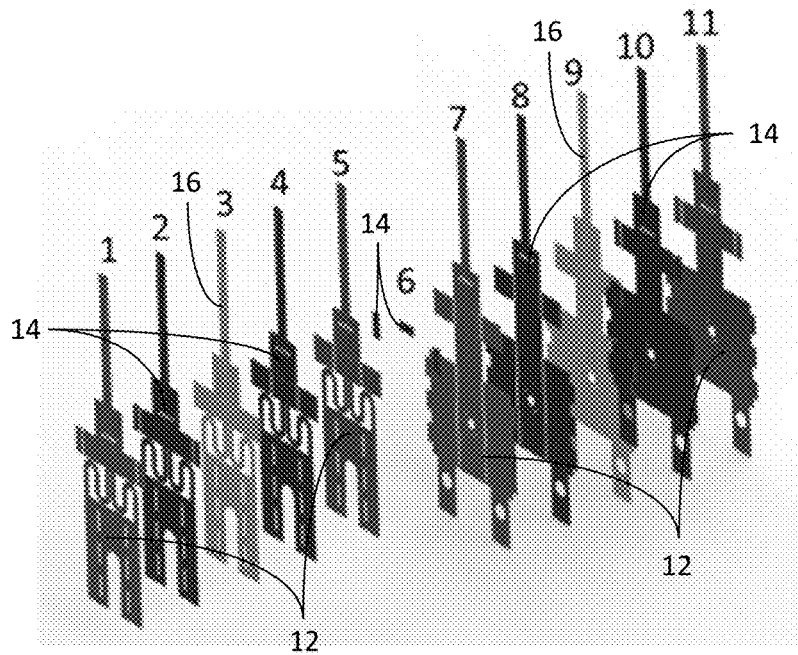
FIG. 11

Laminate Index

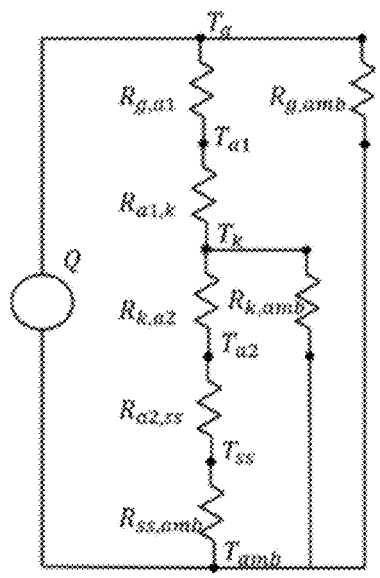
FIG. 20
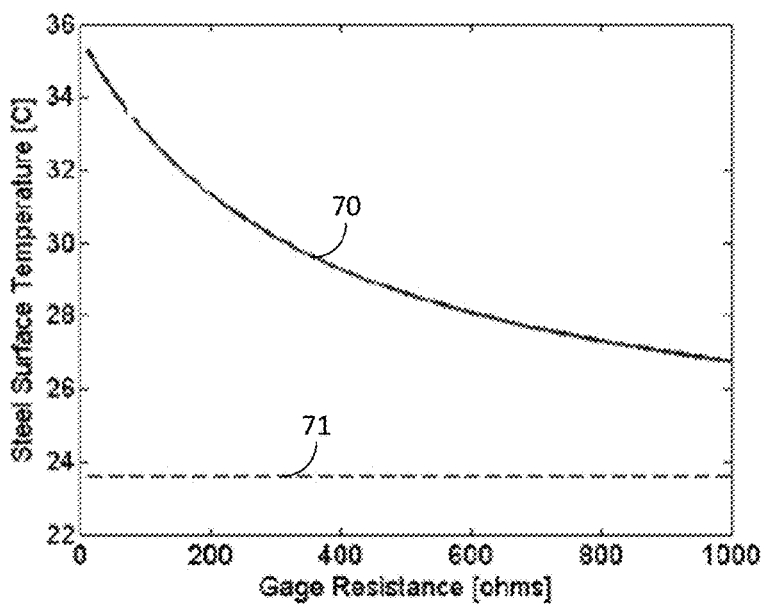
FIG. 21
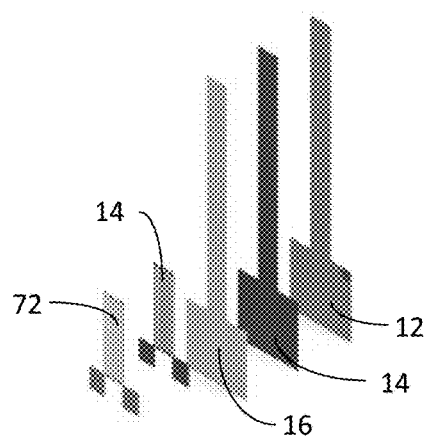
FIG. 22
FIG. 23
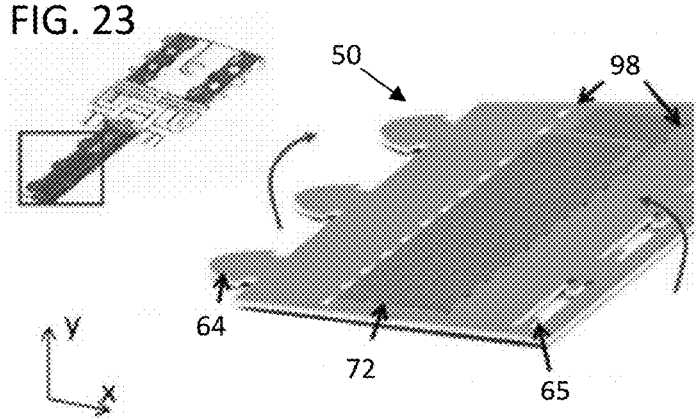
FIG. 24
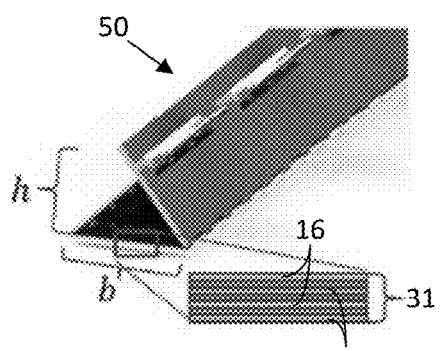
FIG. 25

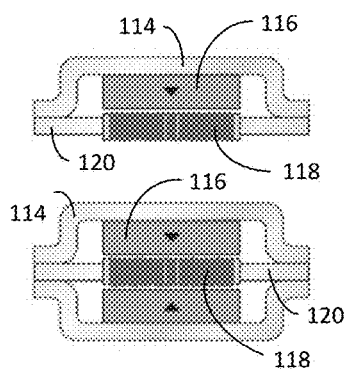
FIG. 39
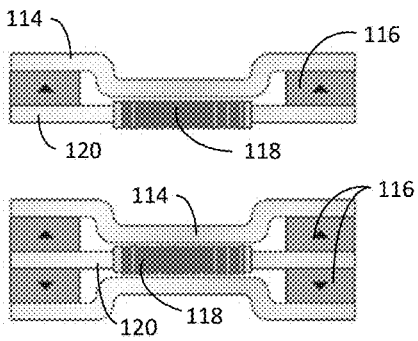
FIG. 40
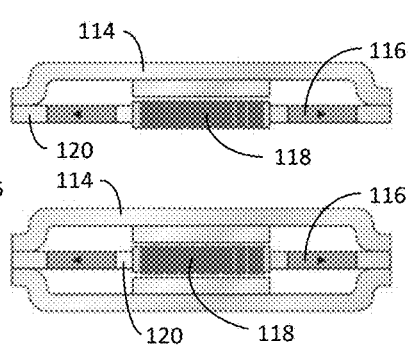
FIG. 41
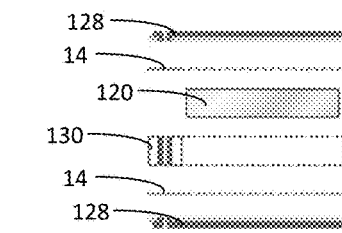
FIG. 42
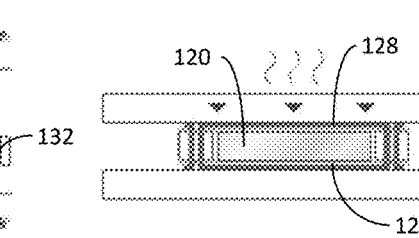
FIG. 43
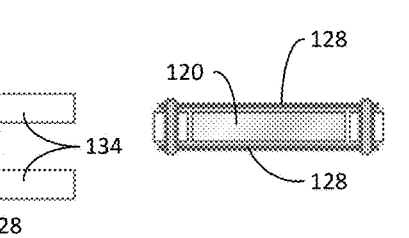
FIG. 44
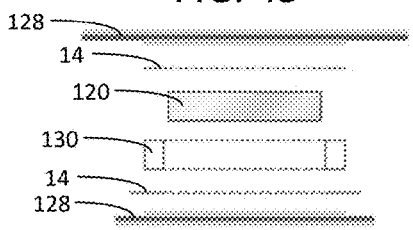
FIG. 45
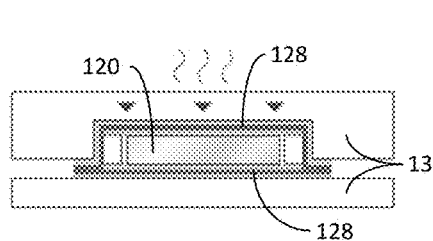
FIG. 46
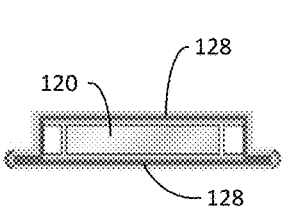
FIG. 47
FIG. 48
FIG. 49
FIG. 50
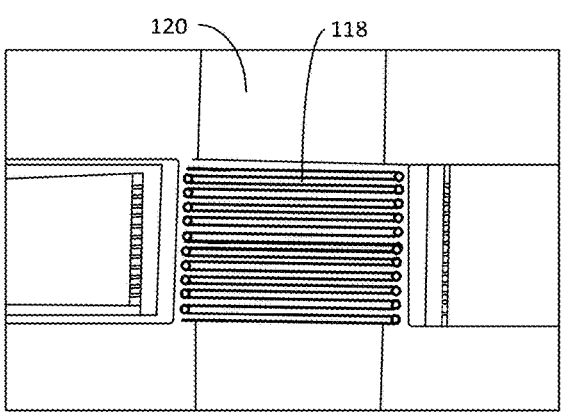
FIG. 51
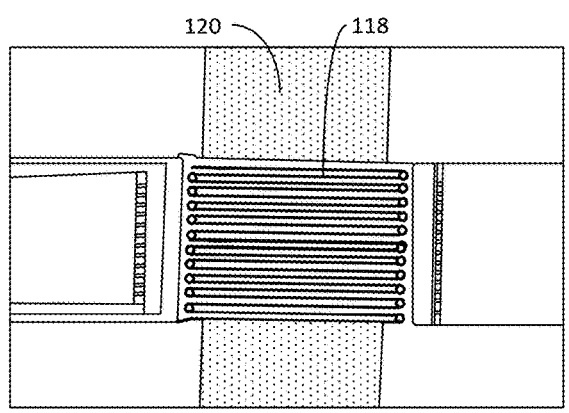
FIG. 52

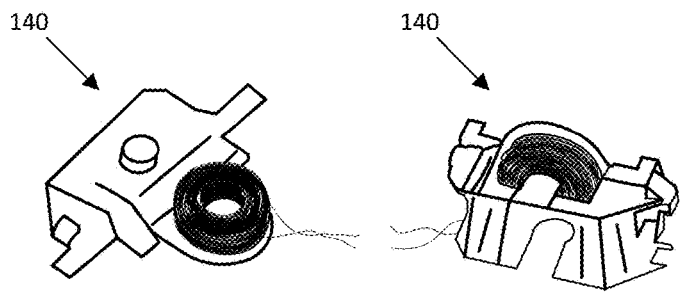
FIG. 58  FIG. 59
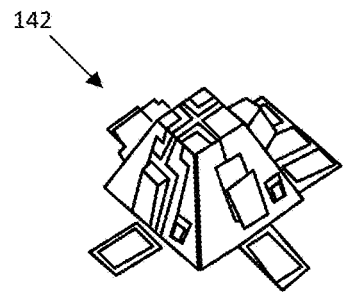
FIG. 60

POP-UP LAMINATE STRUCTURES WITH INTEGRATED ELECTRONICS

RELATED APPLICATION

This application is a continuation of U.S. application Ser. No. 14/909,792 (now U.S. Pat. No. 10,376,326 B2, issued 13 Aug. 2019), which is a national-phase entry of PCT/US2014/049588, filed 4 Aug. 2014. This application also claims the benefit of U.S. Provisional Application No. 61/862,066, filed 4 Aug. 2013. The entire contents of these earlier applications are incorporated herein by reference.

BACKGROUND

Micron-scale device fabrication is dominated by micro-electro-mechanical structures (MEMS) technology, which typically involves a single planar substrate and serial processes. Meanwhile, centimeter-scale manufacturing is covered by a multitude of conventional machining processes. Manufacturing at the millimeter scale, however, is plagued with fabrication and assembly issues that greatly impact the cost and performance of micro-robots and other functional mechanical devices at this scale.

Various pop-up laminate structures are described in priority U.S. Application No. 61/862,066, filed 4 Aug. 2013, which is incorporated by reference herein in its entirety.

SUMMARY

Three-dimensional laminate structures and methods for their fabrication and use are described herein. Various embodiments of the structures and methods may include some or all of the elements, features and steps described below.

In particular embodiments, the layers in the structure can include at least one rigid layer, at least one flexible layer and electrically conductive wiring, wherein the rigid layer includes a plurality of rigid segments, and the flexible layer can extend between the rigid segments to serve as a hinge. The flexible layers are substantially less rigid than the rigid layers, wherein the rigid layer can have a rigidity that is at least twice as great as or an order of magnitude greater than (e.g., at least 10× or 100×) the rigidity of the flexible layer; likewise, the flexible layer can have at least 10 times or at least 100 times the flexibility of the rigid layers. The electrically conductive wiring (traces) extend across the hinges and/or form via structures separating layers in the pop-up laminate.

The layers can then be stacked and bonded at selected locations to form a laminate structure with inter-layer bonds, and the laminate structure can be distorted or flexed to produce an expanded three-dimensional structure, wherein the layers are joined at the selected bonding locations and separated at other locations.

The methods and structures described herein can be used, for example, across and beyond the entire millimeter-scale manufacturing process (e.g., for apparatus with dimensions from 100 µm to 100 mm), and they enable mass production of precisely fabricated mechanisms, machines, and autonomous robots at this scale.

When compared to traditional MEMS, the methods described herein are extremely versatile with respect to the materials that can be used. In addition, traditional MEMS are largely limited to bulk addition of materials, whereas the methods described herein can be used not only to add precisely patterned layers, but also full sub-components, such as integrated circuits, flex circuits, actuators, batteries, etc. The thermal requirements of the multi-layer, super-planar structures described herein can also be much lower, and the fabrication-equipment costs can be much lower, as well. Further still, processing steps in these methods on the various layers can be performed simultaneously in parallel, while much of MEMS processing takes place sequentially in series, resulting in a faster process compared to traditional MEMS.

Also described herein are surgical tools, electrode arrays, magnetic actuators and integrated electronics fabricated using the laminate structures and fabrication techniques described herein, as well as applications thereof.

BRIEF DESCRIPTION OF THE DRAWINGS

FIGS. 8 and 9 are top and side views, respectively, of a serpentine spring pattern from the micro-surgical grasper.

FIG. 10 plots the load as a function of spring extension for a stiff spring and for a compliant spring with respective images of each.

FIG. 11 is an exploded assembly rendering of a grasper prototype.

FIG. 20 is an illustration of an equivalent thermal impedance circuit.

FIG. 21 plots a theoretical model of 304 stainless steel (SS) surface temperature vs. gauge resistance.

FIG. 22 is an exploded view of a gauge layup on the top structural layer of a micro-grasper.

FIGS. 23-25 are illustrations of foldable flaps on a jaw of a grasper to insulate the gauge and to improve the mechanical stiffness of the grasper jaw.

with null force reading, with light contact where the object registers ~100 mN (middle), and with a larger force peaking at nearly 300 mN (right); images of the micro-grasper in each of these three stages are shown above the plot.

Figure 29:
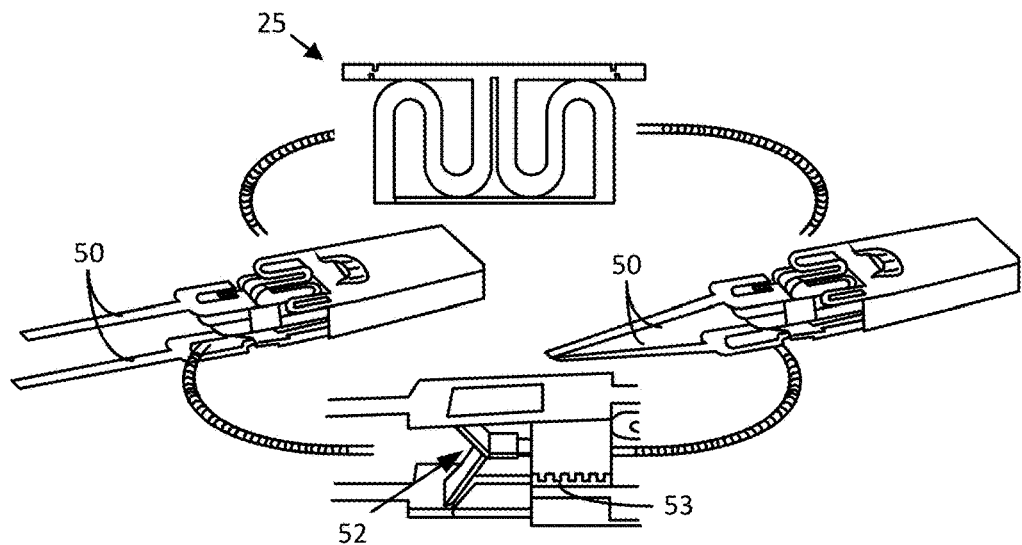

FIG. 29 illustrates actuation of a micrograsper showing the return spring and internal Sarrus linkage detail.

Figure 30:
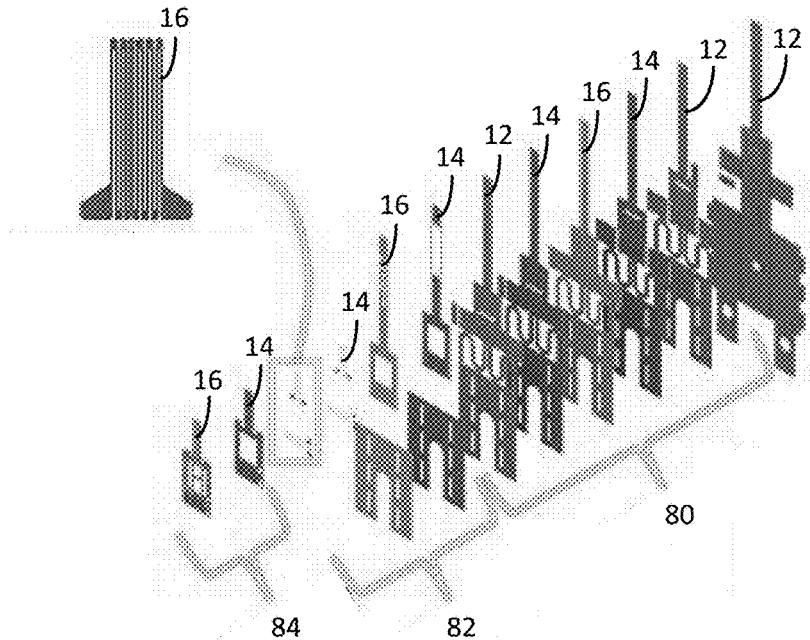

FIG. 30 is an exploded view, showing the layer-by-layer composite manufacture of a micrograsper, incorporating structural, sensing and encapsulation sub-laminates.

Figure 31:
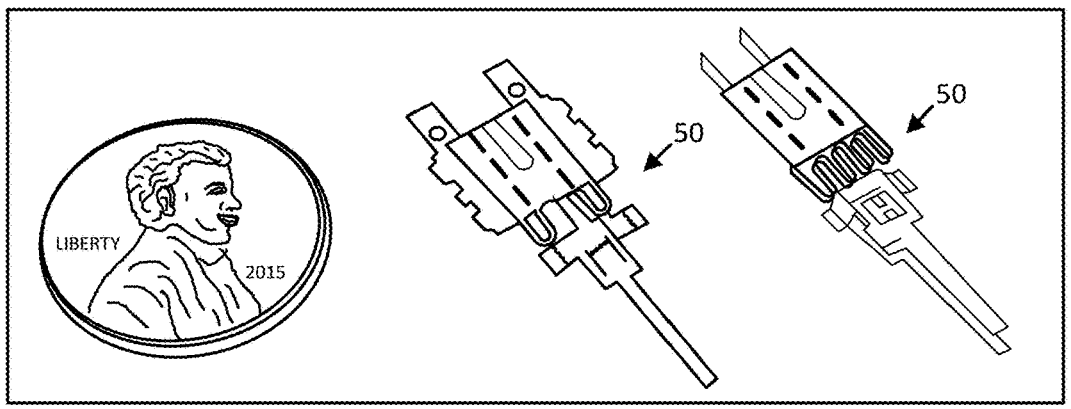

FIG. 31 is a photographic image of an integrated force-sensing micrograsper post-release (middle) and "popped up" (right) with a US penny at left for scale.

Figure 32:
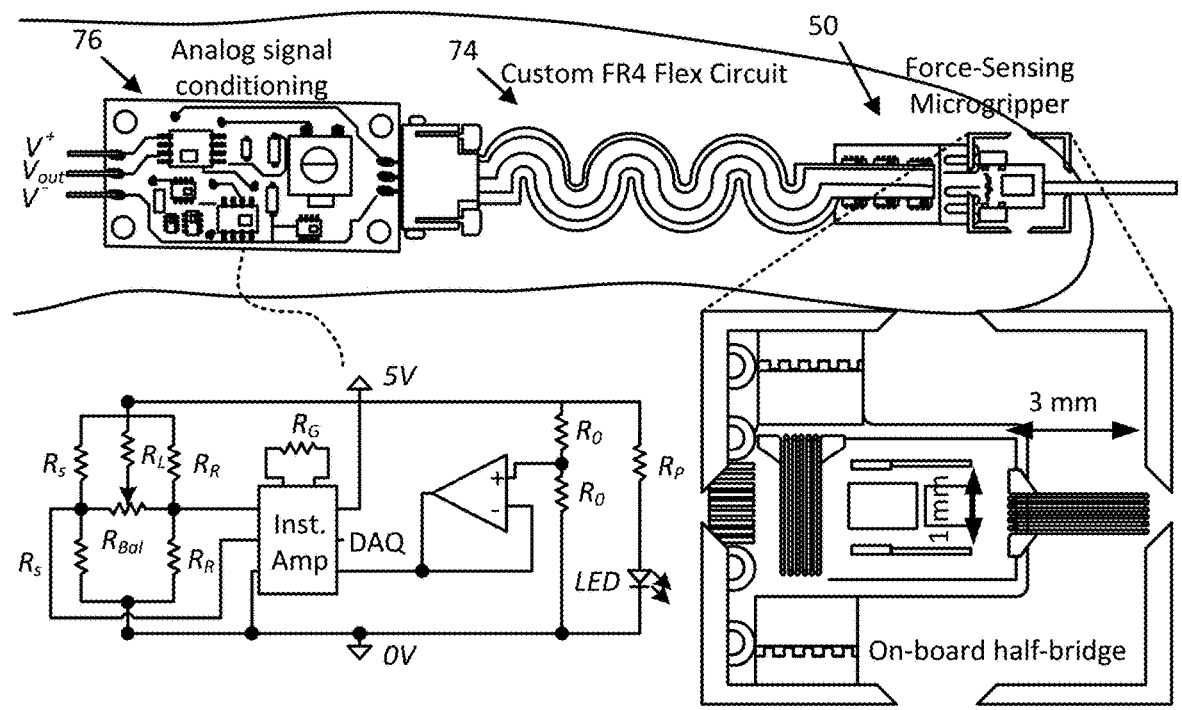

FIG. 32 is a photographic image of a micrograsper and associated flex cabling and conditioning electronics; the completion of an on-board half-bridge, shown in inset, results in thermal stability.

Figure 33:
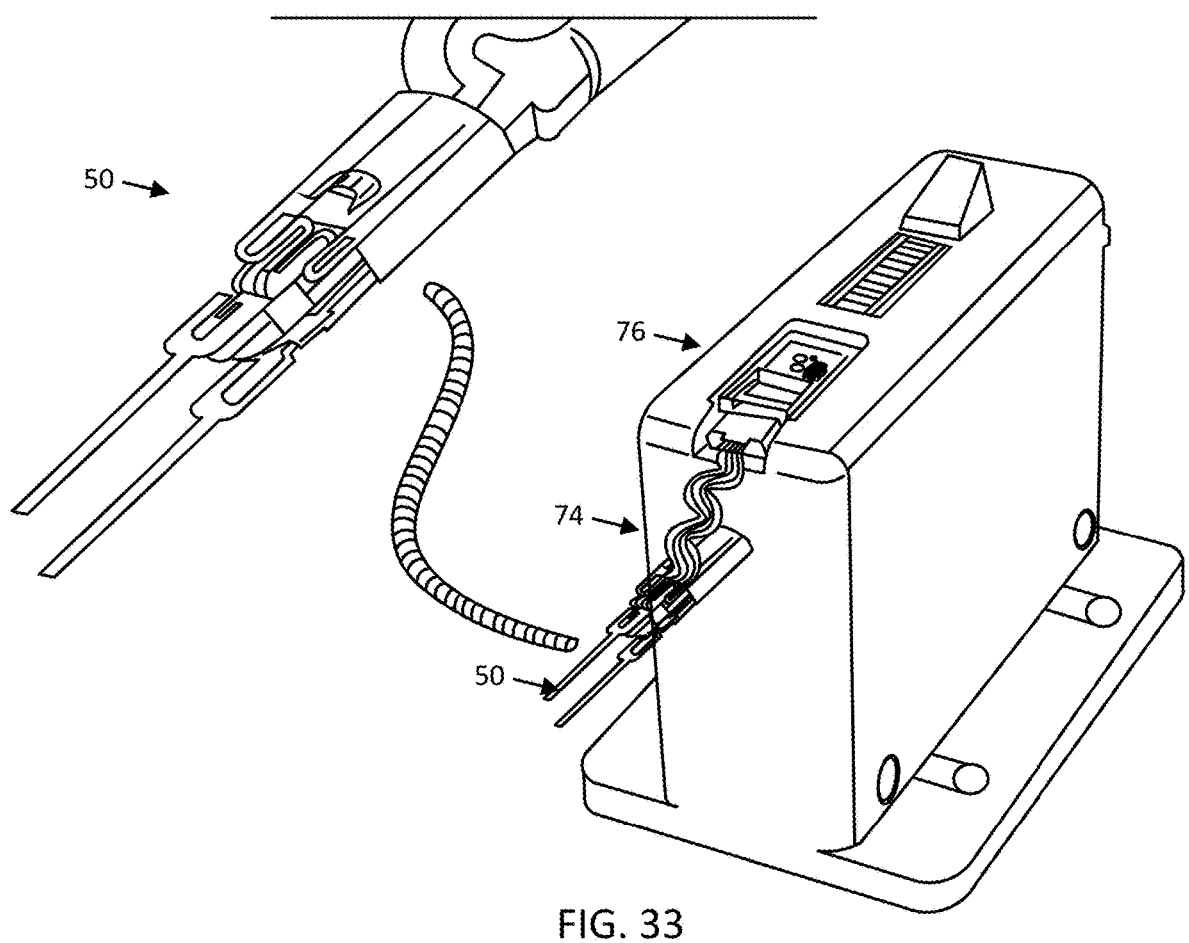

FIG. 33 is a photographic image of a micrograsper integrated into a demonstration platform with real-time visual force-feedback.

Figure 34:
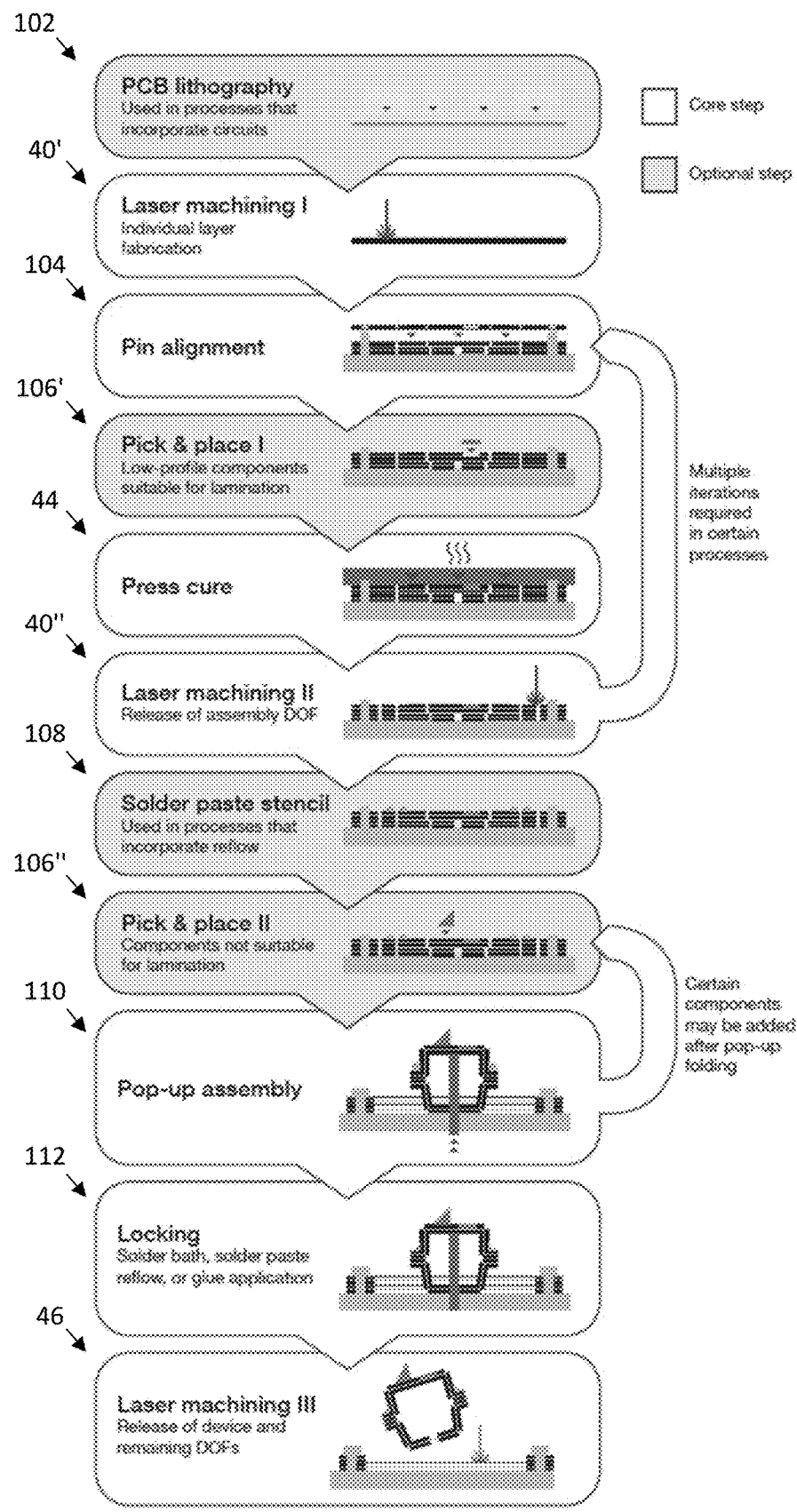

FIG. 34 illustrates a generalized process flow for pop-up MEMS fabrication.

Figure 35:
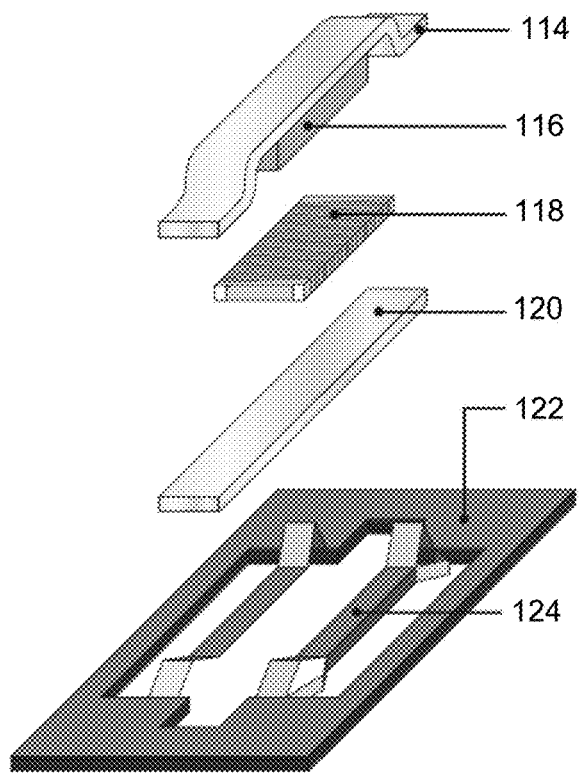

FIG. 35 is an exploded view of a low-profile voice coil actuator (VCA) fabricated via a fabrication process including the steps of FIG. 34.

Figure 27:
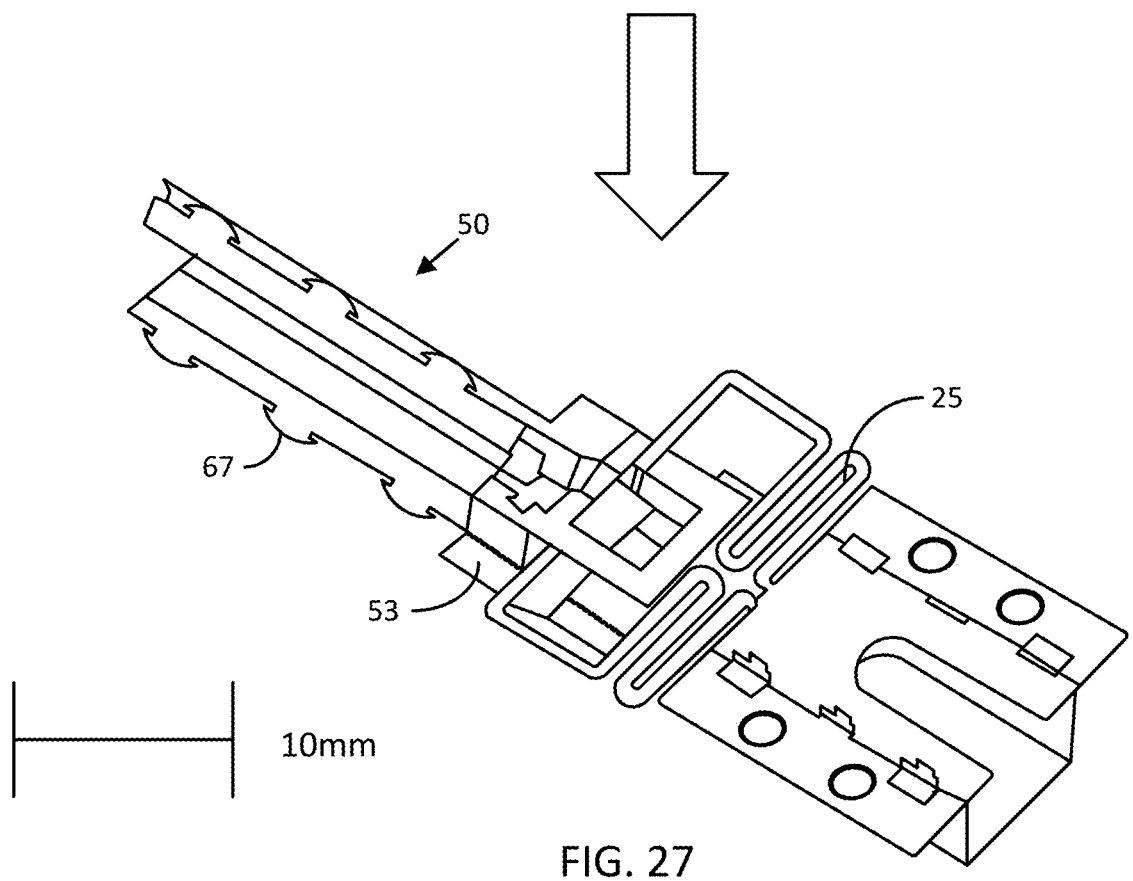
Figure 36:
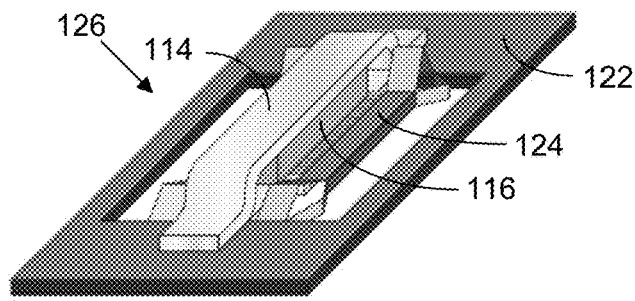

FIG. 36 is an illustration of an assembled VCA device, including the components of FIG. 27 and fabricated via a process of FIG. 34.

Figures 37, 38:
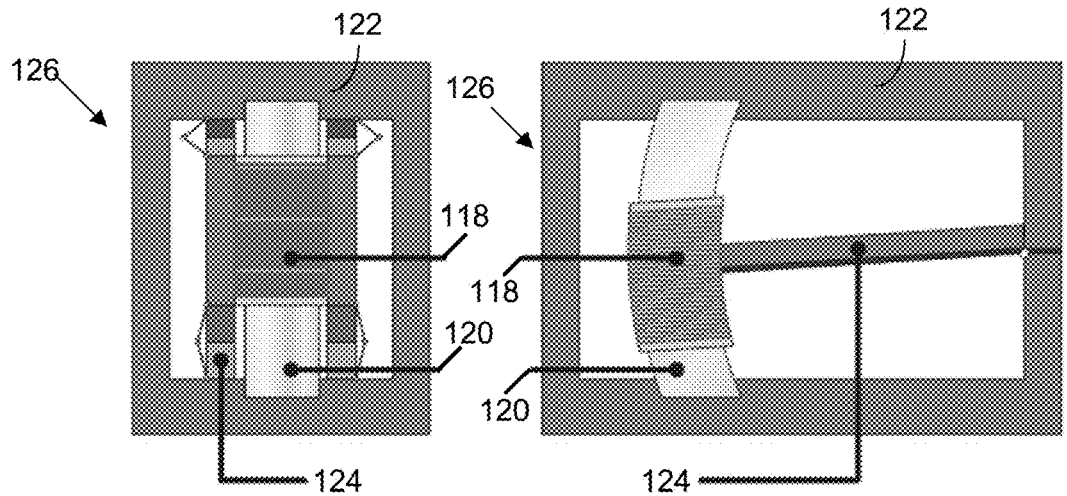

FIGS. 37 and 38, respectively, show a linear and rotary VCA fabricated via a process of FIG. 34.

FIGS. 39-44 illustrate side views of various magnet core arrangements for a VCA (where magnetic polarization is indicated by arrows); the magnetic core is provided on one (top) side of the coil in FIGS. 39-41, while the magnetic core is provided on both (top and bottom) sides of the coil in FIGS. 42-44.

FIGS. 45-47 show a method of VCA fabrication using plated vias, with the components shown in FIG. 45, the lamination step illustrated in FIG. 46, and the VCA after solder immersion or reflow shown in FIG. 47; the coil is shown from a front view, where coil motion would be into and out of the page.

FIGS. 48-50 show a method of VCA fabrication using folding, with the components shown in FIG. 48, the lamination step illustrated in FIG. 49, and the VCA after solder immersion or reflow shown in FIG. 50; the coil is shown from a front view, where coil motion would be into and out of the page.

FIG. 51 is a magnified photographic images of a magnetic coil fabricated using the folding method of FIGS. 48-50 after lamination.

FIG. 52 is a magnified photographic image of the magnetic coil of FIG. 51 after removal of sacrificial features and solder immersion.

Figure 53:
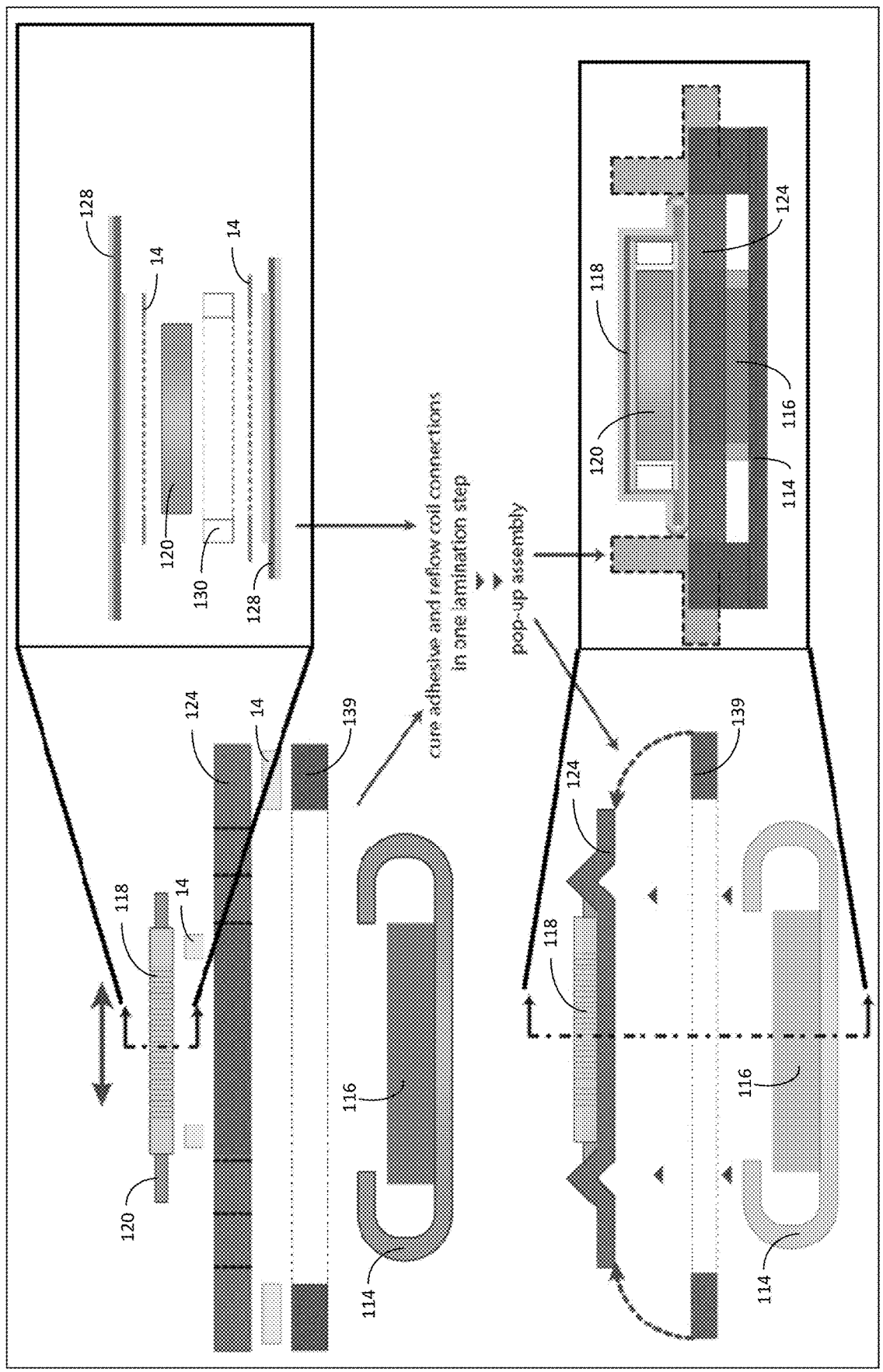

FIG. 53 provides a schematic illustration of the fabrication process for an embodiment of a voice coil actuator (VCA).

Figure 54:
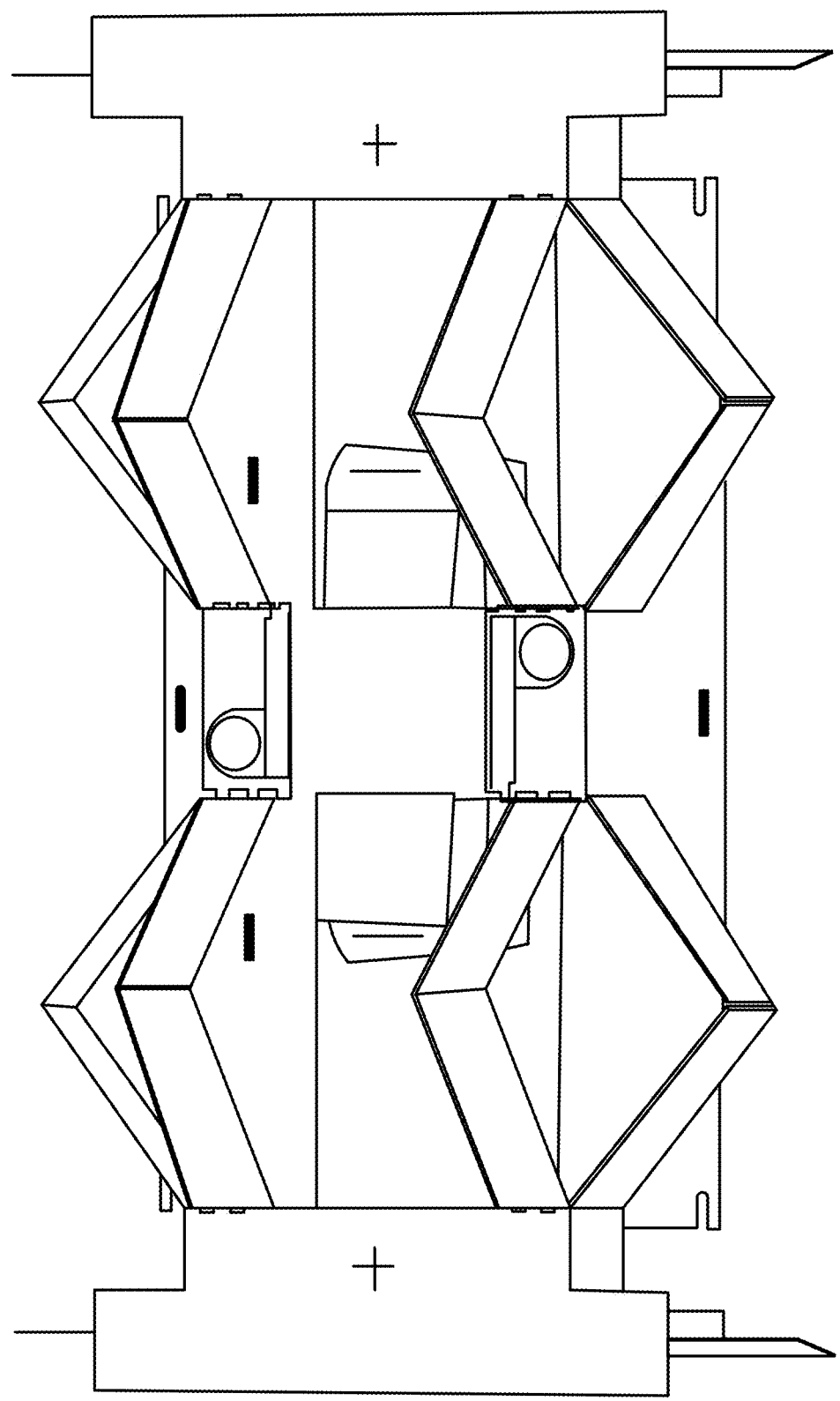

FIG. 54 is a magnified photographic image of an assembled VCA with a Sarrus-linkage based suspension mechanism.

Figure 55:
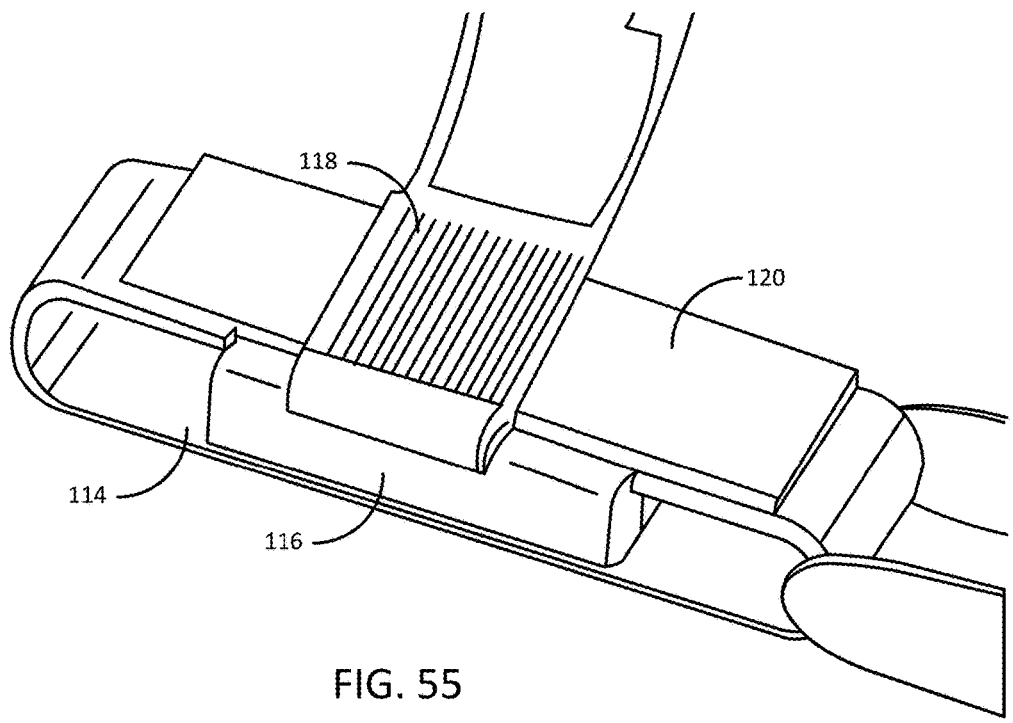

FIG. 55 is a magnified photographic image of an assembled VCA, without the coil constraint mechanisms and surrounding scaffold.

Figure 56:
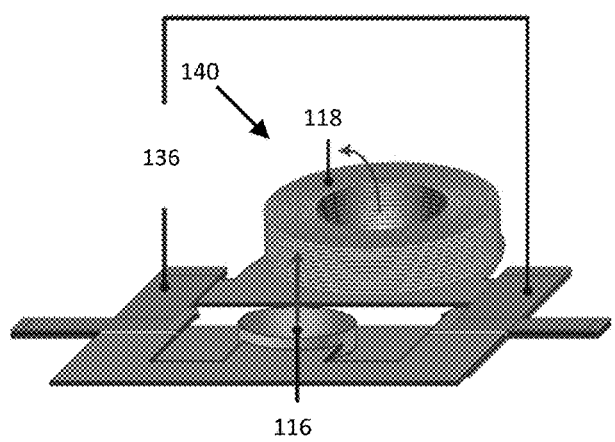
Figure 57:
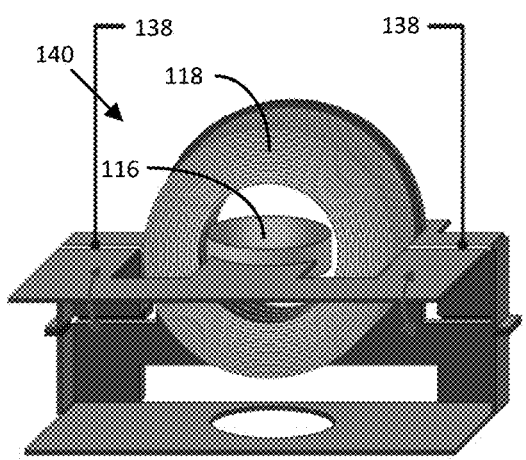

FIGS. 56 and 57 show a pop-up mechanism used to implement a simple rotary actuator; here, the permanent magnet and magnetic coil are prefabricated components positioned on a pop-up MEMS laminate via pick and place.

FIGS. 58 and 59 are photographic images of a simple rotary actuator in pop-up MEMS after lamination and with pick-and-place components attached (FIG. 58) and fully assembled (FIG. 59) adjacent a US penny (0.75 inches in diameter) for an indication of scale.

Figure 61:
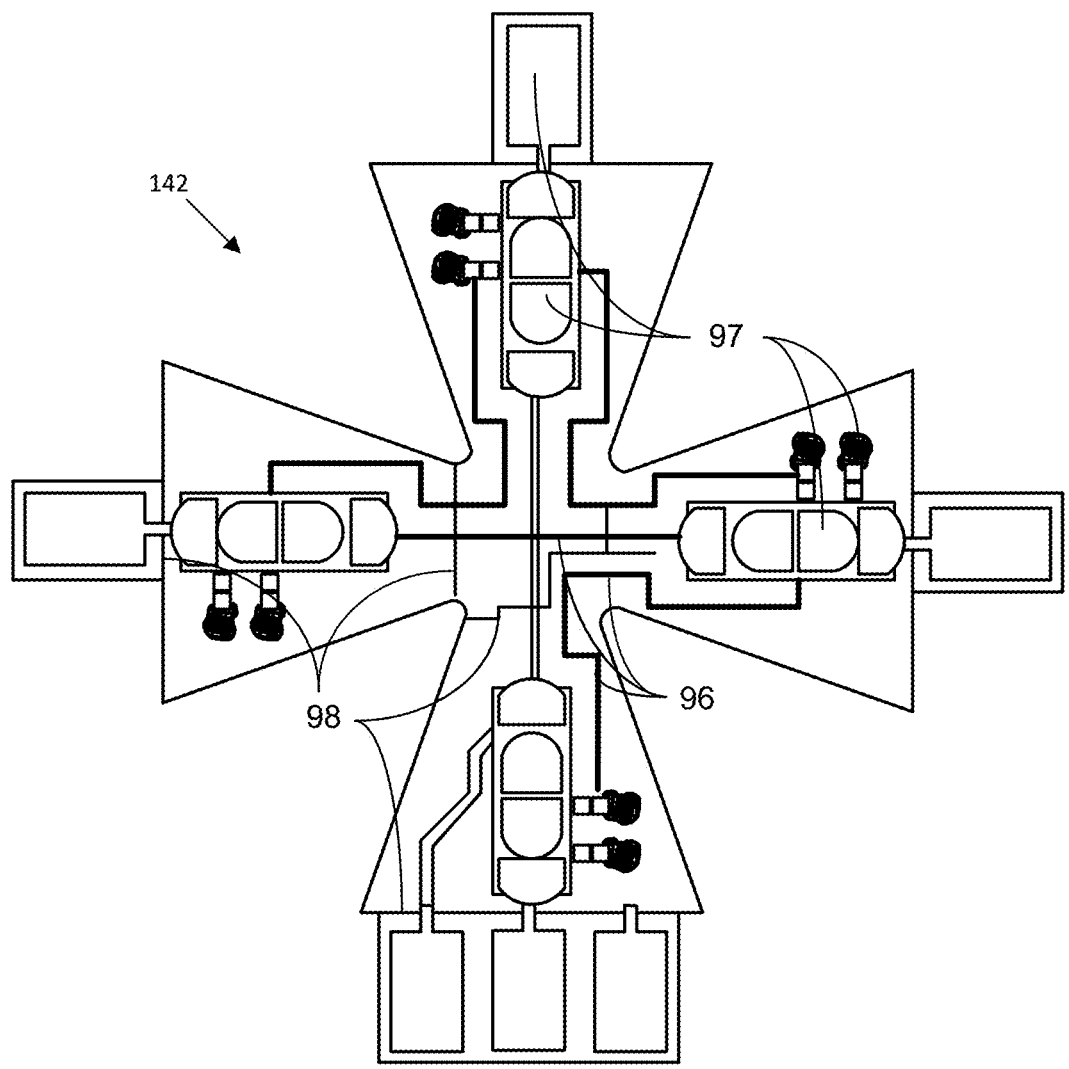

FIGS. 60 and 61 are photographic images of an Ocelli optical sensor composed of rigid and flexible circuits and components and folded into a 3D structure. The US penny (0.75 inches in diameter) provides an indication of scale in FIG. 60.

Figure 62:
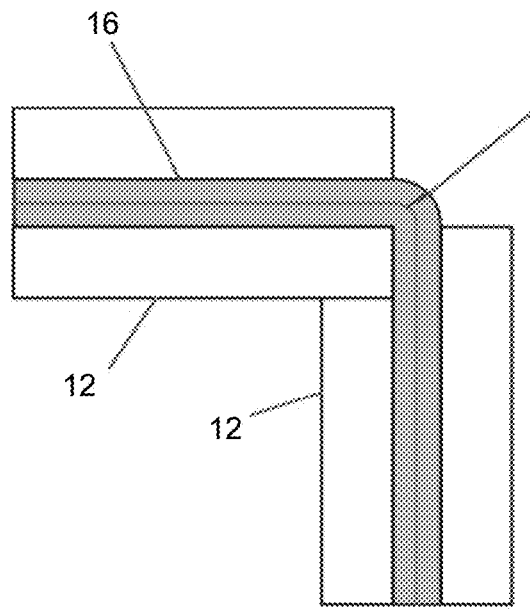

FIG. 62 is a sectional illustration of a small-bend-radius hinge design with the electrical trace embedded in the flexible layer.

Figure 63:
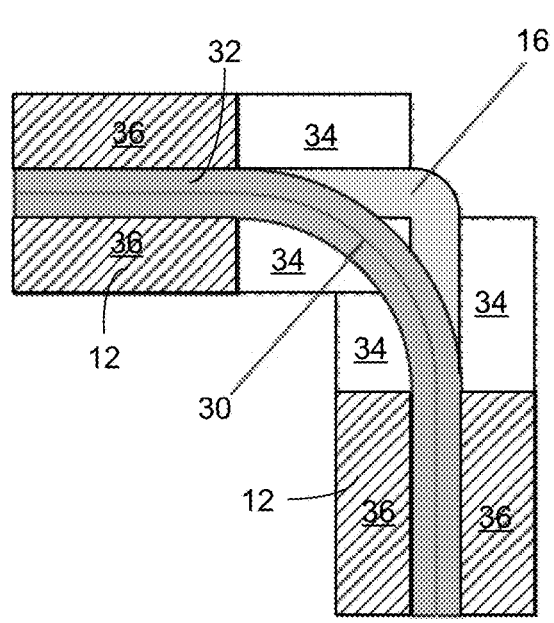

FIG. 63 is a sectional illustration of a hinge design in which the electrical trace is segregated from the small-bend-radius flexible layer via a large-bend-radius cut-out region in the hinge, putting less strain on the electrical trace at the hinge.

Figure 64:
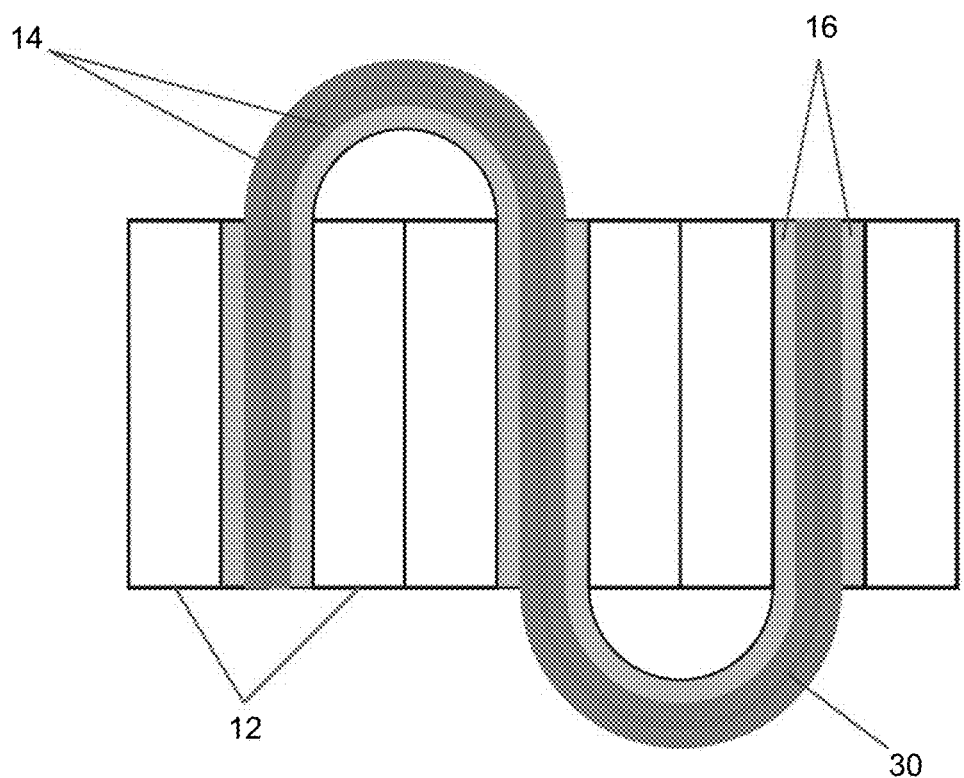

FIG. 64 is an illustration showing the tortuous bending of an electrical trace between rigid layers.

Figure 65:
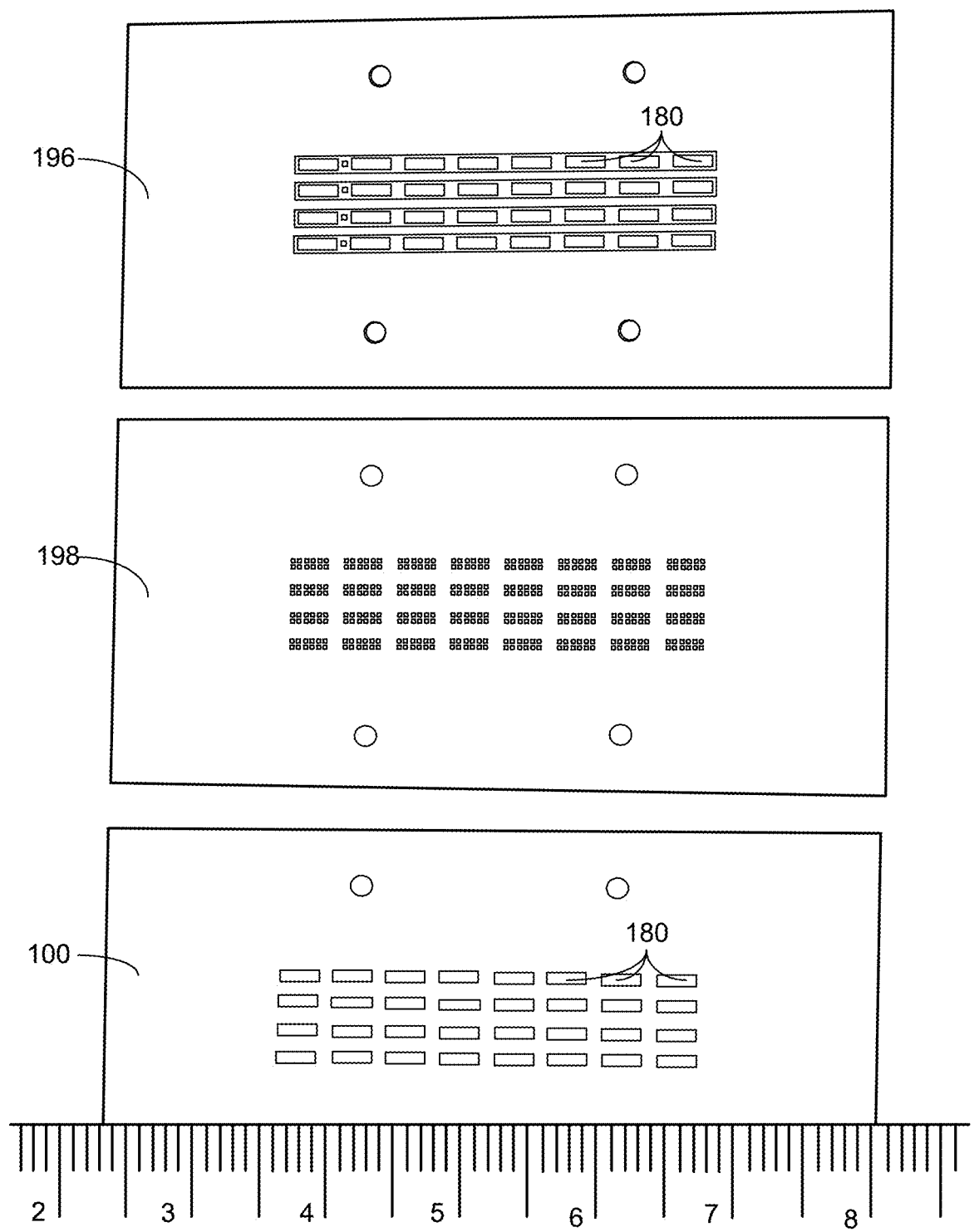

FIG. 65 shows a sequence of added layers to form an embodiment of an electrode panel.

Figure 66:
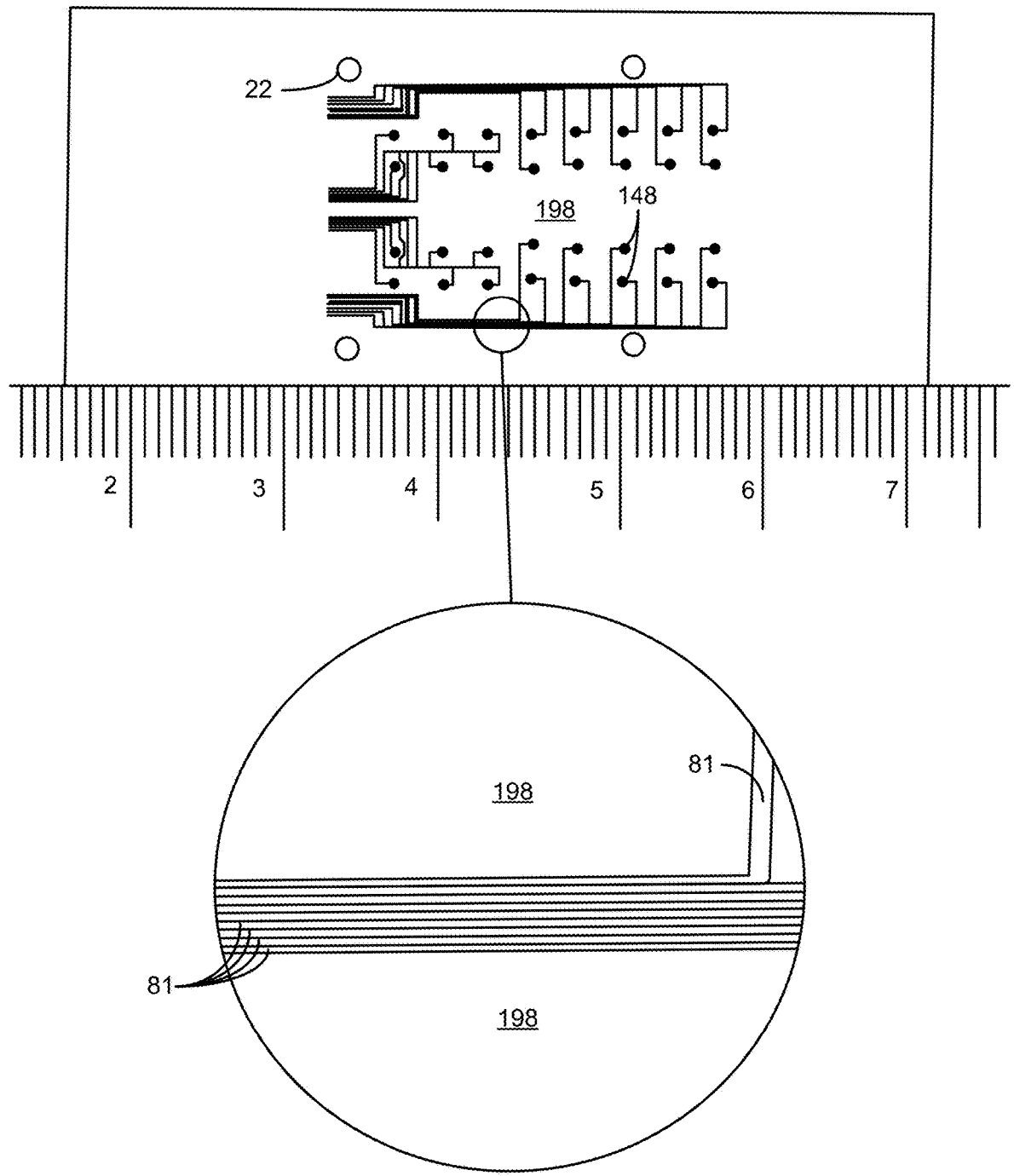

FIG. 66 is a photographic image of a flex circuit layer upon which the electrodes will be mounted to form an electrode panel (top) and a magnified view of the encircled section, provided below, showing the electrical traces in greater detail.

Figure 67:
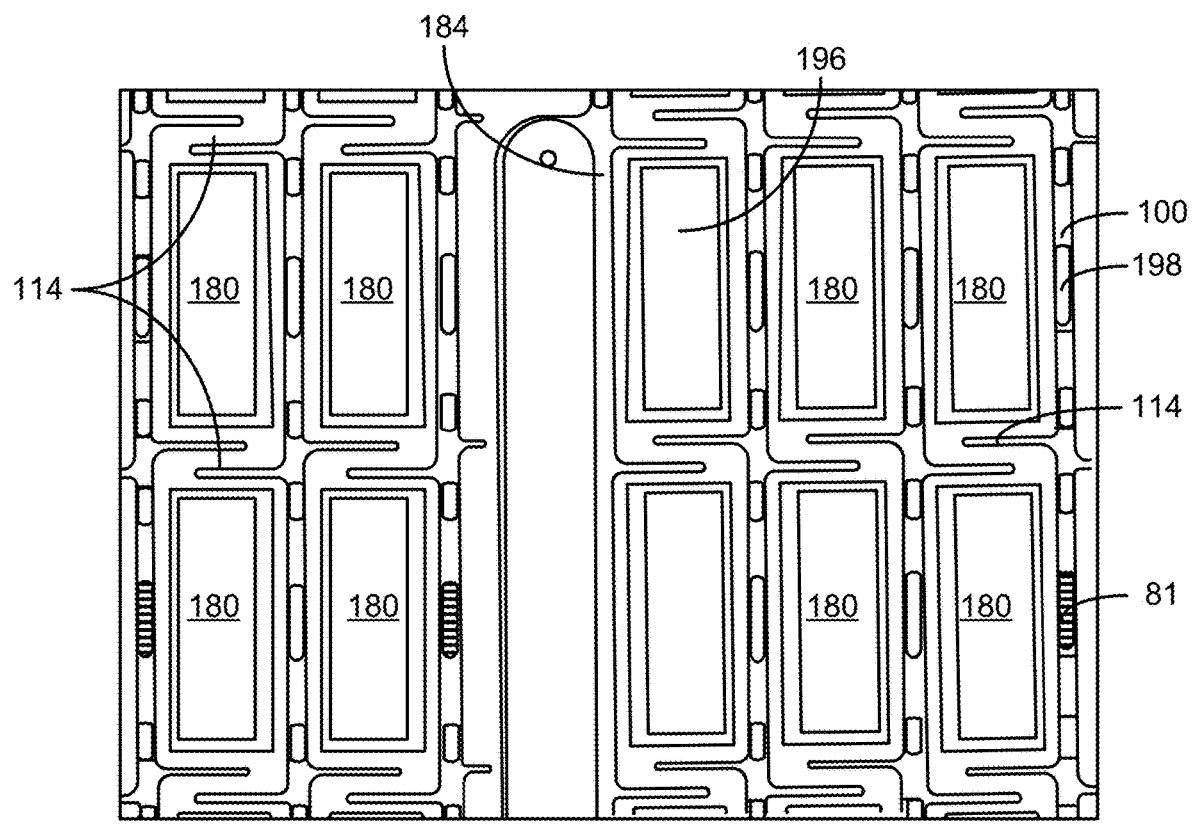
Figure 68:
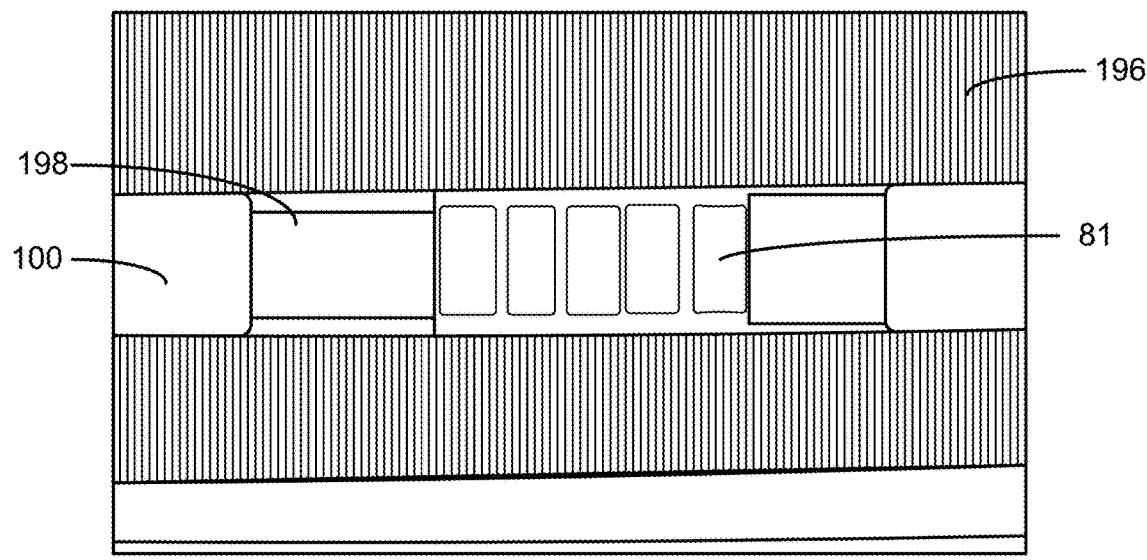

FIGS. 67 and 68 are images of flexible electrical wiring and traces embedded in the deployable electrode structure across hinges and through mechanical components to allow the electrodes to receive signals without the need for external electrical wiring.

Figure 69:
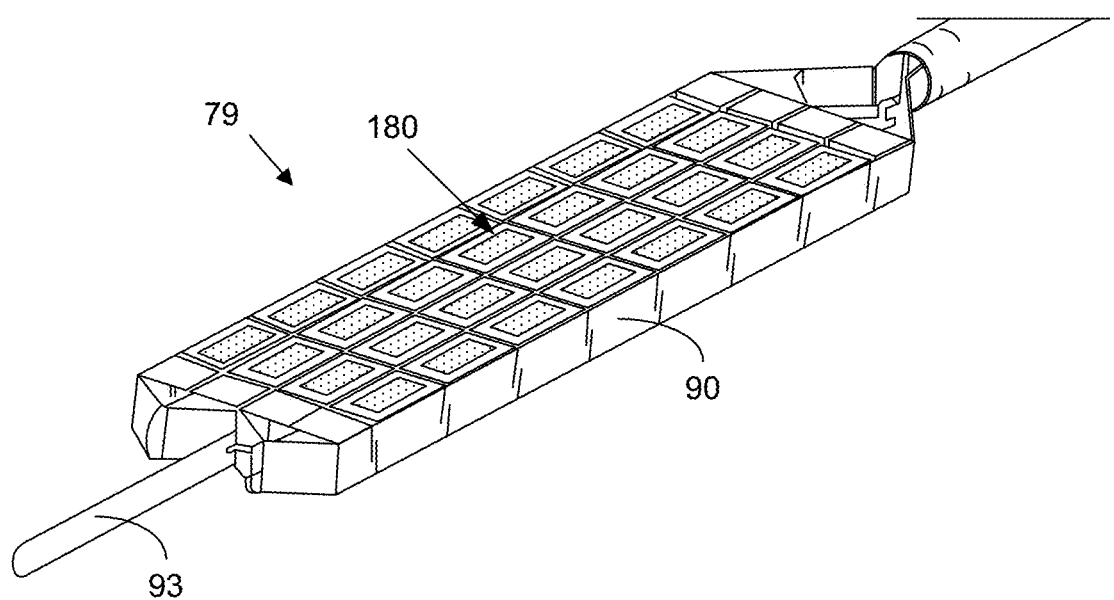

FIG. 69 is an illustration of an embodiment of an expandable and collapsible laminate electrode array with integrated electronics.

In the accompanying drawings, like reference characters refer to the same or similar parts throughout the different views. The drawings are not necessarily to scale, emphasis instead being placed upon illustrating particular principles, discussed below.

DETAILED DESCRIPTION

The foregoing and other features and advantages of various aspects of the invention(s) will be apparent from the following, more-particular description of various concepts and specific embodiments within the broader bounds of the invention(s). Various aspects of the subject matter introduced above and discussed in greater detail below may be implemented in any of numerous ways, as the subject matter is not limited to any particular manner of implementation. Examples of specific implementations and applications are provided primarily for illustrative purposes.

Unless otherwise defined, used or characterized herein, terms that are used herein (including technical and scientific terms) are to be interpreted as having a meaning that is consistent with their accepted meaning in the context of the relevant art and are not to be interpreted in an idealized or overly formal sense unless expressly so defined herein. For example, if a particular composition is referenced, the composition may be substantially, though not perfectly pure, as practical and imperfect realities may apply; e.g., the potential presence of at least trace impurities (e.g., at less than 1 or 2%) can be understood as being within the scope of the description; likewise, if a particular shape is referenced, the shape is intended to include imperfect variations from ideal shapes, e.g., due to manufacturing tolerances.

Percentages or concentrations expressed herein can represent either by weight or by volume.

Although the terms, first, second, third, etc., may be used herein to describe various elements, these elements are not to be limited by these terms. These terms are simply used to distinguish one element from another. Thus, a first element, discussed below, could be termed a second element without departing from the teachings of the exemplary embodiments.

Spatially relative terms, such as "above," "below," "left," "right," "in front," "behind," and the like, may be used herein for ease of description to describe the relationship of one element to another element, as illustrated in the figures. It will be understood that the spatially relative terms, as well as the illustrated configurations, are intended to encompass different orientations of the apparatus in use or operation in addition to the orientations described herein and depicted in the figures. For example, if the apparatus in the figures is turned over, elements described as "below" or "beneath" other elements or features would then be oriented "above" the other elements or features. Thus, the exemplary term, "above," may encompass both an orientation of above and below. The apparatus may be otherwise oriented (e.g., rotated 90 degrees or at other orientations) and the spatially relative descriptors used herein interpreted accordingly.

Further still, in this disclosure, when an element is referred to as being "on," "connected to," "coupled to," "in contact with," etc., another element, it may be directly on, connected to, coupled to, or in contact with the other element or intervening elements may be present unless otherwise specified.

The terminology used herein is for the purpose of describing particular embodiments and is not intended to be limiting of exemplary embodiments. As used herein, singular forms, such as "a" and "an," are intended to include the plural forms as well, unless the context indicates otherwise. Additionally, the terms, "includes," "including," "comprises" and "comprising," specify the presence of the stated elements or steps but do not preclude the presence or addition of one or more other elements or steps.

The apparatus can be a multi-layer, super-planar structure. The planar structure includes a layer or plane that can be distorted, flexed or folded (these terms may be used interchangeably herein). An embodiment of this structure can be achieved, for example, by forming a five-layer composite with the following sequence of laminated layers: rigid layer, adhesive layer, flexible layer, adhesive layer, and rigid layer. Alternatively, a thinner composite can be formed from a stacking of just a rigid layer, an adhesive layer, and a flexible layer, though this structure is not symmetric. The rigid layers are machined to have gaps that correspond to fold lines, while the flexible layer is continuous, thereby providing a joint where the flexible layer extends across the gaps machined from the rigid layers. The dimensions and feature sizes of the various apparatus described herein can be, e.g., 0.1 mm to 5 cm or, in more particular embodiments, 0.5 mm to 2 cm. Moreover, the devices described, below, can be mass-fabricated by forming a plurality of the laminate structures across a large-area multi-layer laminate from which the individual devices can then be popped by, e.g., severing sacrificial bridges that joint the devices to the rest of the large-area laminate.

Characterization of the structure as being "super-planar" means taking multiple planar layers and selectively connecting them. An analogy here can be drawn to circuit boards, where electrical vias connect circuits on different layers. Here, in contrast, the structure is made with "mechanical vias." By stacking multiple planar layers, the range of achievable devices is greatly expanded. The super-planar structure also enables features and components to be packed into the structure that would not fit if the device could only be made out of one planar sheet. Advantageously, super-planar structures with mechanisms that operate normal to the plane can now be made with these techniques. In practice, forming Sarrus linkages between planar layers is an advantageous strategy for designing an assembly mechanism/scaffold. Other mechanisms can attach to the Sarrus linkages to effect component rotations.

Figure 1:
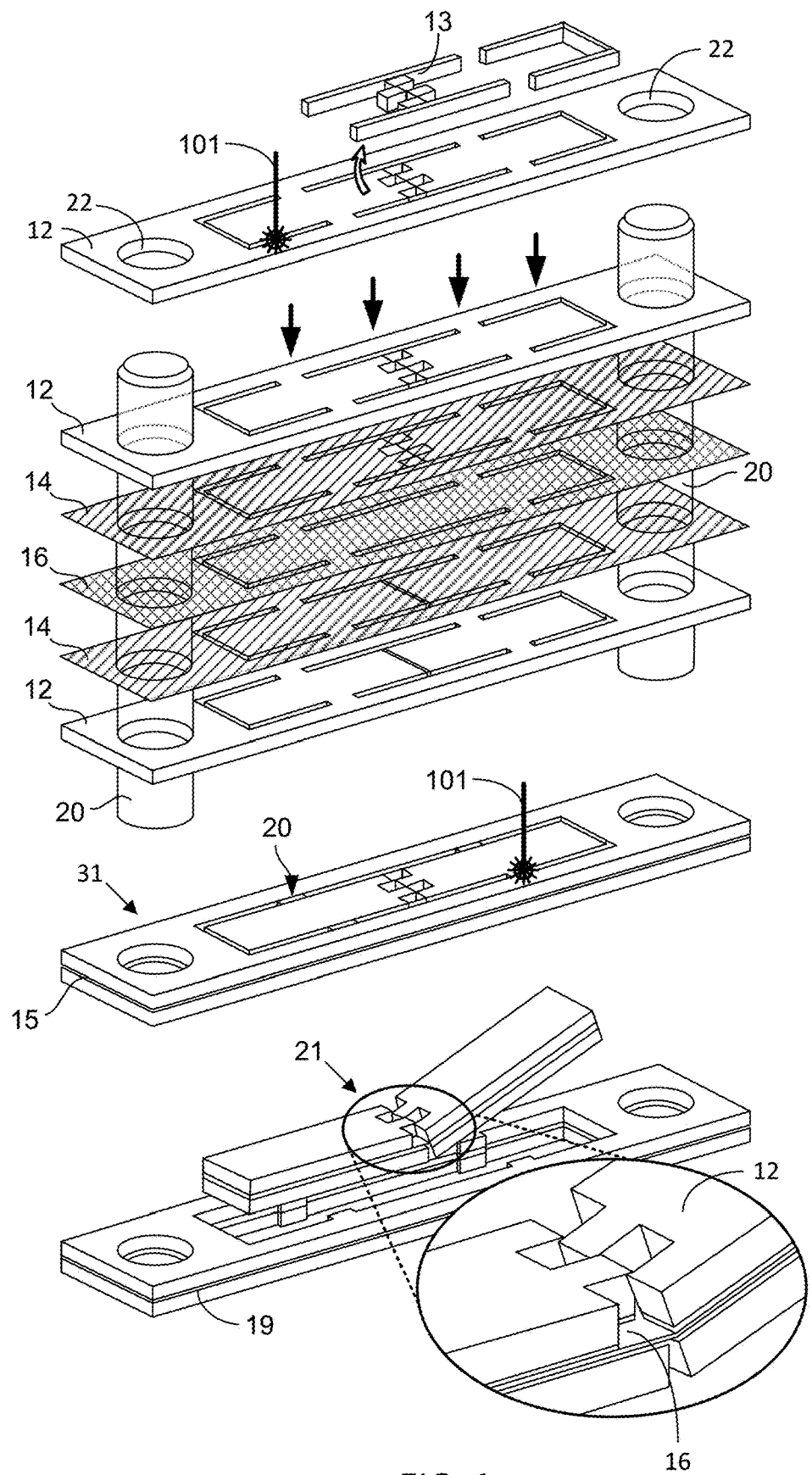
FIG. 1 illustrates a sequence of steps in the formation of folding joints.

The fabrication of a multi-layer expandable structure is shown in FIG. 1 and can include the formation of folding joints 21, wherein (a) features are first micro-machined 101 in individual material layers, and the resulting chips 13 are removed; (b) during lamination, dowel pins 20 align material layers while heat and pressure are applied; here, two rigid carbon-fiber layers 12 bonded to a flexible polyimide-film layer 16 with adhesive 14 form a five-layer laminate 15 referred to as a "linkage sub-laminate"; (c) micro-machining cuts mechanical bridges 17 that constrain individual elements, allowing the creation of articulated structures; and (d) a completed folding joint 21 is formed and removed from the surrounding scaffold 19. The castellated pattern allows this flexure joint 21 to approximate an ideal revolute joint. All assembly folds in a more-complex assembly can be incorporated into a single "pop-up" degree of freedom, which can be locked in place by a soldering process after pop up and then released by micro-machining.

Polyimide can have a flexural modulus of about 20 GPa; other materials (e.g., polymers) with a flexural modulus with a flexibility within about, e.g., 25%, 50% or 75% of this value (higher or lower) can alternatively be used for the flexible layer. The rigid layers can be, e.g., less than half as flexible (i.e., more than twice as stiff as the flexible layer.

1) Machining of Layers

Figure 2:
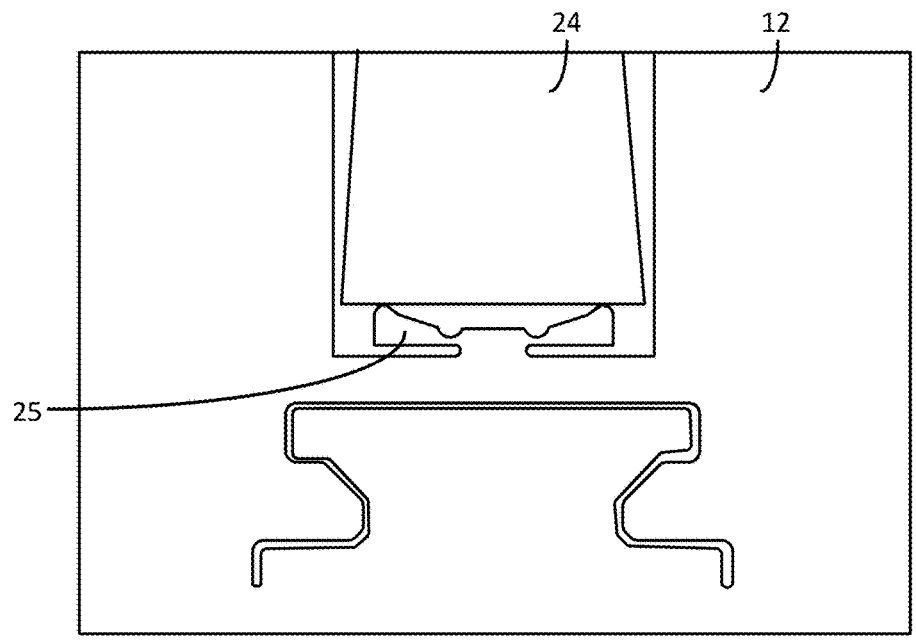
FIG. 2 is a close-up photographic view of the spring clip holding the actuator in place.

In one embodiment, the multi-layer structure is formed from a multitude of thin (1.5-μm to about 150-μm thick) layers of various materials The layers can be laser micro-machined (e.g., by a diode-pumped solid-state pulsed laser) with desired features, usually cutting all the way through the layer to create individual planar structures, as shown, e.g., in FIG. 2. Each layer is micro-machined so as to leave a unified (contiguous) part with robust connections to surrounding alignment holes. The micro-machining can produce complex in-plane features with dimensions as small as 10 μm. In particular embodiments, many copies of the devices are formed on a laminate panel, and the machining process removes sufficient material to form each part and part feature, while leaving thin tabs to connect each device to the surrounding laminate; in this regard, the arrangement of devices in a laminate panel can be similar to that of a batch of circuit boards attached to a surrounding laminate structure by thin, easily breakable tabs.

In this case, the tabs (bridges) 17 (shown in stages a-c of FIG. 1) connecting the devices to the surrounding laminate will be removed after lamination or assembly. Layers of metal, composite, polymer, etc., are machined or formed by virtually any method; and virtually any material may be used. Exemplary machining methods include laser cutting from sheet material, photo-chemical etching, punching, electroforming, electric discharge machining, etc.—basically any method that has appropriate resolution and compatibility with the desired material. Machined layers may then be subjected to additional processes, such as cleaning/etching to remove machining debris, plating (e.g., plating fluxed copper on a layer to facilitate adhesion of solder thereto), preparation for bonding, annealing, etc. The unified nature of each layer makes handling and post-processing easy. Advantageously, each layer can be a different material and can be machined and treated differently from each of the other layers.

Each layer can also advantageously be formed of a material that is sufficiently rigid, strong and tough to allow holes 22 for alignment pins 20 and other features to be machined into the layer, to facilitate easy handling, and to not distort when placed into the layup and when restrained by alignment pins 20. In other embodiments, layers that do not have the structural stability to support alignment features can nevertheless be used by attaching such layers, in bulk form, to a rigid frame that meets these objectives without introducing enough additional thickness to disturb the other layers or parts in the laminate.

In particular examples, a very thin polymer film (e.g., 2-5 microns thick) is included among the layers. Due to its thinness and insulating qualities, the thin polymer film is prone to wrinkling and electrostatic handling issues. To address this tendency, the thin polymer film can be lightly stretched, in bulk form, to a flat and controlled state and then bonded to a thin frame that is made, for example, of thin metal or fiberglass composite. Next, the thin polymer layer can be machined with the fine part features (e.g., tiny holes in the polymer at precise locations), and the alignment hole features can be machined into the frame material.

In additional embodiments, the device can be designed to mitigate thin-layer handling issues. For example, a part within the device can be designed such that all machining pertinent to a fragile layer is performed post-lamination; and, thus, this layer will not require precision alignment when put into the laminate, though the material is advantageously capable of being placed into the laminate sufficiently flat and extending over a sufficient area to cover the desired parts of the device.

In exemplary embodiments, bulk polymer films (formed, e.g., of polyester, polyimide, etc.); metal sheets and foils [formed, e.g., of stainless steel, spring steel, titanium, copper, invar (FeNi36), nickel-titanium alloy (nitinol), aluminum, etc.]; copper-clad laminates; carbon fiber and glass fiber composites; thermoplastic or thermoset adhesive films; ceramic sheets; etc.; can be laser machined to make the layers that are laminated to form the multi-layer structure. The laser machining can be performed, e.g., with a 355-nm laser (from DPSS Lasers Inc. of Santa Clara, Calif.) with a spot size of about 7 microns on materials with typical thicknesses of 1-150-μm, although thicker layers can be machined with such a laser, well. Accordingly, this type of laser allows for very high resolution and an ability to machine almost any type of material.

2) Machining or Patterning Adhesives

Adhesion between layers is achieved by patterning adhesive onto one or both sides of a non-adhesive layer or by using free-standing adhesive layers ("bondplies") 14. In the latter case, an intrinsically adhesive layer 14, e.g., in the form of a sheet of thermoplastic or thermoset film adhesive, or an adhesive laminate, such as a structural material layer with adhesive pre-bonded to one or both sides, is used. The adhesive layer 14 is machined like the other layers. Specific examples of sheets that can be used as the adhesive layer 14 include sheet adhesives used in making flex circuits (e.g., DuPont FR1500 adhesive sheet) or polyimide film 16 coated with FEP thermoplastic adhesive 14 on one or both sides. Free-standing sheet adhesives can be acrylic-based for thermosets; alternatively, the adhesive can be thermoplastic, wherein the thermoplastic film can be formed of polyester, fluorinated ethylene propylene (or other fluoropolymer), polyamide, polyetheretherketone, liquid crystal polymer, thermoplastic polyimide, etc. Any of these adhesives can also be applied on one or both sides to a non-adhesive carrier. In additional embodiments, a layer may serve both as a structural layer 12 and as a thermoset adhesive 14—for example, liquid crystal polymer or thermoplastic polyimide. Furthermore, for special types of structural layers, a variety of wafer bonding techniques that do not require an adhesive may be employed, such as fusion bonding.

In another technique for achieving adhesion between layers, adhesive 14 is applied and patterned directly on a non-adhesive layer 12. This technique can be used where, for example, the type of adhesive desired may not be amenable to being in a free-standing form. Examples of such an adhesive 14 include solders, which are inherently inclined to form a very thin layer, or adhesives that are applied in liquid form (by spraying, stenciling, dipping, spin coating, etc.) and then b-stage cured and patterned. B-staged epoxy films are commonly available, but they usually cannot support themselves unless they are quite thick or reinforced with scrim.

The resulting bond can be a "tack bond," wherein the adhesive 14 is lightly cross-linked to an adjacent layer before laser micromachining with sufficient tack to hold it in place for subsequent machining and with sufficient strength to allow removal of the adhesive backing layer. The tack bonding allows for creation of an "island" of adhesive 14 in a press layup that is not part of a contiguous piece, which offers a significant increase in capability. Another reason for tacking the adhesive 14 to an adjacent structural layer is to allow for unsupported "islands" of adhesive 14 to be attached to another layer without having to establish a physical link from that desired adhesive patch to the surrounding "frame" of material containing the alignment features. In one embodiment, a photoimagable liquid adhesive, such as benzocyclobutene, can be applied in a thin layer, soft baked, and then patterned using lithography, leaving a selective pattern of adhesive. Other photoimagable adhesives used in wafer bonding can also be used.

The adhesive 14 is patterned while initially tacked to its carrier film, aligned to the structural layer 12 using pins 20, and then tacked to at least one adjoining layer in the layup with heat and pressure (e.g., at 200° C. and 340 kPa for one hour). Alternatively, the adhesive layer can be patterned by micro-machining it as a free sheet. Tack bonding can involve application of heat and pressure at a lower intensity and for less time than is required for a complete bond of the adhesive. In yet another embodiment, the adhesive film 14 can be tack bonded in bulk, and then machined using, for example, laser skiving/etching. Advantageously, use of this variation can be limited to contexts where the machining process does not damage the host layer. Both of these variations were tried using DuPont FR1500 adhesive sheet and laser skiving.

3) Stacking and Laminating the Layers

To form the multi-layer laminate structure, a multitude of these layers are ultrasonically cleaned and exposed to an oxygen plasma to promote bonding and aligned in a stack by passing several vertically oriented precision dowel pins 20 respectively through several alignment apertures 22 in each of the layers, and by using a set of flat tooling plates with matching relief holes for the alignment pins 20. In other embodiments, other alignment techniques (e.g., optical alignment) can be used. All layers can be aligned and laminated together.

Linkages in the laminated layers can be planar (where all joint axes are parallel); or the joint axes can be non-parallel, allowing for non-planar linkages, such as spherical joints.

Where the flexible layers 16 are bonded to rigid segments 12 and extend across the gaps between the rigid segments 12), they enable flexure of the rigid segments 12 relative to one another at the flexible layer 16 in the gaps between the rigid segments 12. Accordingly, the exposed sections of the flexible layer 16 effectively serve as joints. In particular embodiments, the "rigid" layers 12 comprise carbon and "flexible" layers 16 are formed of polyimide.

The choice of the flexible layers 16, which can be formed of a polymer—polyimide in this example—is based upon compatibility with the matrix resin in the carbon fiber. The cure cycle can reach a maximum temperature of 177° C. using a curing profile of four hours. Polyimide film (available, e.g., as KAPTON film from E.I. du Pont de Nemours and Company), for example, has a sufficiently high service temperature (up to 400° C.) to survive the curing step. The polyimide film can have a thickness of, e.g., 7.5 µm.

The rigid layers 12 in this embodiment are standard cured carbon fiber sheets (e.g., with three layers of unidirectional fibers, wherein the fiber layers are oriented at 0°, 90°, and 0° to provide thickness in two orthogonal directions) having a thickness of, e.g., 100 µm.

After the layers are stacked to form the layup, pressure and heat are applied, typically in a heated platen press to cure/crosslink the adhesive layers. Specifically, the layup can be cured in a heated press, autoclave, or other device that provides the atmosphere (or lack thereof), temperature, and pressure to achieve the bonding conditions required by the adhesive. One embodiment of the curing process uses 50-200 pounds-per-square-inch (psi) clamping pressure, 350° F. (177° C.) temperature, and two-hours cure time (optionally with temperature ramping control) to cure DuPont PYRALUX FR1500 acrylic sheets in a heated press with temperature, pressure, and atmosphere control.

4) Post-Lamination Machining

The laminate 31 is then machined (e.g., by severing tabs with a laser) to release the device(s) from a surrounding frame structure in the laminate 31. In some embodiments, additional machining that is not involved with freeing the device from the external frame (circumscribing the device in the laminate 31) is reserved for after lamination (e.g., post-lamination machining of a layer that is structurally weak or that, for some other reason, cannot be precisely aligned since the weak layer is better supported after lamination).

5) Post-Lamination Treatment

A post-lamination treatment can include plating or coating on an exposed layer. Additional components may be attached to the laminate 31 using a pick-and-place methodology. Pick-and-place operations can be used to insert discrete components into layups before press lamination.

For example, a stimulus responsive material 24, such as an electroactive material, can be inserted among the layers to serve as an actuator. In one embodiment, a lead zirconate titanate piezoelectric plate 24 is mounted on a spring clip 25 in the carbon layer 12 (shown in FIG. 2) and has been demonstrated to create a functional bimorph cantilever actuator within a device. A broad range of discrete components can be inserted this way, such as mirrors or other optical components, micro-electro-mechanical systems (MEMS), discrete sensors, etc. These components may alternatively be added earlier—e.g., before lamination at some point in the stack-up process—or they can be added after the subsequent assembly of the device.

6) Freeing the Assembly Degree of Freedom in Each Part

The resulting laminate can then be laser micro-machined and/or scrap materials can be removed from the laminate to "release" functional components in each part. The parts, as laminated, may unfold to have many actuated and passive mechanical degrees of freedom; though, in some embodiments, restraining these non-assembly degrees of freedom during the assembly folding process is advantageous. For example, elements of a flexural linkage can be held in place (i.e., locked)—to prevent the linkages from flexing—by a rigid bar element alongside the elements or by a fixed tab forming an integral bridge between the elements and the surrounding structure. Using a machining process (e.g., punch die or laser cutting), the tabs or other features that restrain the assembly degree of freedom are severed.

7) Assembly

As fabricated, the device can be a flat multi-layer laminate with limited three dimensional structure. Its components undergo a variety of assembly trajectories to realize the final fully three-dimensional topology. A co-fabricated mechanical transmission called an "assembly scaffold" can couple all of these assembly trajectories into a single degree of freedom. The device can emerge from the manufacturing process as a three-degree-of-freedom machine, though internal mechanical connections may eliminate these active degrees of freedom during assembly. The resulting mechanism can use, e.g., over a hundred folding joints to assume a fully three-dimensional topology in one motion, similar to those created by paper folding in pop-up books.

Assembly of the final device (including unfolding of the linkages into multiple planes) can be performed manually by external actuation, or assembly can happen spontaneously. Where assembly is spontaneous, if one or more of the layers is pre-strained, the relaxation of the pre-strained layers can lead to the assembly of the device as soon as the assembly degree of freedom is freed. The layer that is pre-strained can be, for example, a patterned spring formed of spring steel or another spring-capable material, such as a superelastic nickel titanium alloy (nitinol) or an elastomer material that can survive the lamination conditions without annealing or degradation. The dowel pins and the pin alignment holes in the pre-strained layer can be configured to maintain this tension when the pre-strained layer is in the stack through lamination. The pre-strain can be in the form, for example, of tension or compression, though compression may require consideration of tendencies of linkages to buckle out of plane.

In other embodiments, actuators can be built into the laminate to effect assembly. For example, a piezoelectric bending actuator, shape memory layer, or other type of actuator can be laminated into the structure as a pick-and-place component or inserted as an integral part of a layer in the layup; and the actuator can be actuated, e.g., by supplying electrical current or by changing temperature, to assemble the expanded structure of the device. In one embodiment, the actuator is a bimorph cantilever including two 127-µm nickel-plated lead zirconate titanate (PZT) piezoelectric plates (PSI-5H4E, Piezo Systems, Inc.) coated with chromium to provide protection during the downstream locking process and bonded to a central carbon-fiber layer. Quasi-kinematic mating features and planar spring clips in the carbon-fiber layer 12 or titanium layer 41 can hold each plate in alignment during lamination.

Advantageously, in some embodiments, the assembly of all parts is actuated via a single assembly degree of freedom so that assembly proceeds in parallel for an entire panel, rather than part by part. Assembly can be effected in several ways, depending on the design and complexity of the part. For example, a human operator can actuate the assembly degree of freedom manually or semi-automatically. In one embodiment, the assembly degree of freedom is in the form of a plate connected to a Sarrus linkage that is pulled up or pushed down. Spherical joints or four-bar mechanisms can be attached to the Sarrus linkage, raising and folding other components into their three-dimensional position. Note that by having multiple rigid-flex planar layers and selective adhesion, complex mechanisms and collections of mechanisms can be released in the assembly step.

Pop-up MEMS relies on the lamination of multiple material layers. After bulk machining and prior to the initial lamination step, these layers typically are contiguous (with the exception of b-staged adhesive layers, where tack bonding may be used to form islands). In certain cases, it may be desirable to create non-contiguous layers (e.g., to create an array of isolated electrodes, electrical wiring machined from conductive foils, or other objects). In this case, a pressure-sensitive transfer material, such as GEL-PAK tape (from Gel-Pak of Hayward, Calif., US) or certain types of pressure-sensitive adhesive tape, can be used to maintain the geometry of the non-contiguous layer prior to and during lamination.

8) Joint Locking of Assembled Part

After assembly into a final three-dimensional structure, structural members can be bonded together in a fixed configuration (i.e., locked, fixed or frozen). In one embodiment, adhesive can be manually applied to structural members and/or joints, though this approach may not be ideal if many parts are being made. Alternatively, adjacent members that have come together to form a locked joint can be automatically laser welded. If adjacent members have metal pads 47 (e.g., formed of brass) on them, then wave or dip soldering can form strong filleted bonds between the members. Alternatively, solder paste can be applied, for example, by screen printing before assembly to the laminate; and then, after assembly, a re-flow step in a hot oven creates the bonds. Other variations include the use of two-part adhesives, etc.

After folding, pads on disparate links align into "bond points," in the form of either two pads 47 meeting at right angles or three pads forming the corner of a cube. The structure, held in its folded state, is submerged in a water soluble flux (e.g., Superior Supersafe No. 30) and then pre-heated in an oven at 100° C. for 10 minutes. It is then submerged in 260° C. tin-lead eutectic solder for approximately 1 second. Finally, the structure is ultrasonically cleaned in distilled de-ionized water to remove the water-soluble flux residue. The result of this soldering process is the formation of solder fillets at all bond points, eliminating the assembly degree of freedom and locking all disparate machine components together.

9) Freeing the Non-Assembly Degrees of Freedom

Any non-assembly degrees of freedom in the part can be unlocked by removing any features (e.g., connected tabs) that restrain them via, e.g., laser machining.

10) Separating Parts from the Scrap Frame

Now that the individual parts are fully assembled and ready for operation, the parts can be separated from the scrap frame (e.g., an outer frame to which the parts are connected by bridges of material) of the scaffold 19 by laser machining, punching, etc.

Pop-Up MEMS-Enabled Minimally Invasive Surgical Tools

The small scale of microsurgery poses significant challenges for developing robust and dexterous tools to grip, cut, and join sub-millimeter structures, such as vessels and nerves. The main limitation is that traditional manufacturing techniques are not optimized to create smart, articulating structures in the 0.1-10 mm scale. Pop-up micro electromechanical systems (MEMS) offer means for overcoming this challenge and enabling the monolithic fabrication of complex, articulated structures with an extensive catalog of materials, embedded electrical components, and automated assembly with feature sizes down to 20 microns.

Figure 6:
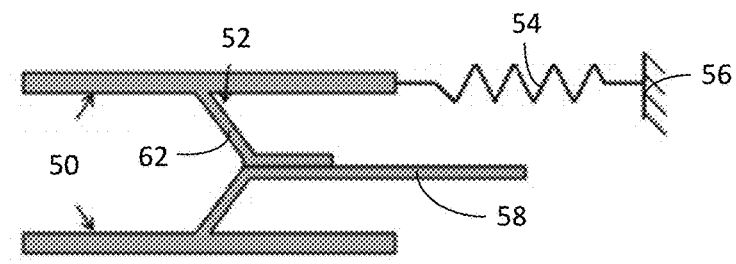
FIGS. 6 and 7, respectively, are open and closed functional illustrations of a micro-surgical grasper.
Figure 7:
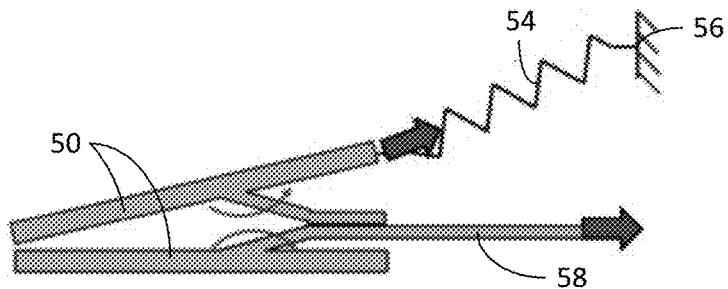

The grasper devices described herein are fabricated with pop-up MEMS fabrication technology. As shown in FIGS. 6 and 7, the grasping tool can include two jaws 50 that open and close in either a parallel or angulated (like tweezers) motion. The jaws 50 can be fabricated to any size and opening distance. Particular embodiments have 20×2 mm and a 10×1 mm jaw sizes, with a 4 mm and a 3 mm jaw opening size, respectively.

Force sensors can be embedded into the jaws 50 to show the magnitude of the force. One embodiment uses integrated metal foil-based strain sensing. Particular embodiments are actuated via a proximal cable drive or other form of mechanical linkage, although the device can alternatively be distally actuated with an embedded or connected motor (e.g., incorporated into the device at the pivot point for the jaws), such as a piezoelectric element, a shape memory alloy, hydraulic or pneumatic actuators, or a traditional electromagnetic motor. The minimally invasive surgery (MIS) grasper can also be fabricated with additional articulation, such as movable wrist mechanisms.

In additional embodiments, the pop-up fabrication technology allows for direct integration of any of the following: return springs, flexural mechanisms, actuators or mechanical actuation pull cables, 3D structural components assembled out of 2D materials, and combinations thereof. The fabrication process can also be used to create biomedical grade grasper devices using biocompatible materials and adhesives.

In addition to manipulation, other specific embodiments of this approach include cutting or resecting tools for trimming material, such as tissues inside a joint or torn ligaments; connecting tools, such as mm-scale staplers, suturing devices or vessel sealers; a microbiopsy tool for taking tissue samples, including multiple samples with the same tool and samples from constrained areas.

Final assembly of the device can be completed during the fabrication process. The device "pops-up" using the alignment scaffold designed into the entire lamination layup that is ultimately discarded. Alternatively, the final assembly can be achieved after the device is inserted into the workspace environment (e.g., a clean room for a micro-assembly task or into the body for a surgery) by manually or automatically popping-up into its final configuration independent of any assembly scaffold, such as the way a pop-up tent operates.

Exemplary applications in which these graspers can be employed include (a) assembly of micro-meso scale mechanisms, such as the Harvard monolithic robotic bee (mobee) or mechanical watch mechanisms; (b) microsurgery, such as sub-millimeter nerve and vessel anastomosis required to reattached digits or limbs; (c) gripping, palpating or cutting tissue during laparoscopic surgery; (d) small joint arthroscopic surgery, where an articulated microtool is inserted into a joint to help remove torn tissues, implant grafts, or reconstructs damage structures; and (e) allowing for percutaneous introduction of tools into the body by allowing grasper or other tools to collapse down, be passed through a needle, and then "pop-up" into a final 3D shape inside the body.

Specific advantages that can be provided by embodiments of the grasper device include the following. First, electronics (e.g., sensors, actuators) can be integrated directly or in parallel into the manufacturing, allowing for fabrication of customized sensors and actuators based on functional requirements with negligible additional manufacturing overhead. Second, for monolithic manufacturing, all components can be manufactured and assembled using the same process. No additional assembly, especially of the type that requires precise alignment of sensors with mechanical part features, is required. Third, for flexural-enabled motion, no pins or sliding joints are required for articulation, which minimizes or completely eliminates friction and wear. Fourth, laser machining allows for smaller features than those that are achievable via conventional machining processes (e.g., down to 20 microns with the current system). Fifth, traditional structural materials (e.g., plastics, metals, carbon fiber) can be used to make meso- and micro-scale devices. Multiple materials can be integrated and laminated into a single, monolithic structure using this method. Sixth, sensing, on-board actuation, and articulated components, such as wrists, can be integrated into micromanipulation tools. Seventh, the collapsible geometry of the device allows for insertion through smaller incisions or access ports.

This section demonstrates a proof-of-concept microsurgical grasper and evaluates its performance at the component and device level to characterize its strength and robustness. One-degree-of-freedom (1-DOF) flexible hinge joints that constrain motion and allow for out-of-plane actuation were found to resist torsional loads of 22.8±2.15 N—mm per mm of hinge width. Adhesive lap joints that join individual layers in the laminate structure demonstrated a shear strength of 26.8±0.53 N/mm². The laminate structures were also shown to resist peel loads of 0.72±0.10 N/mm². The above values are based on the actuation mechanism, materials used, and the size of the device; accordingly, different values can be achieved by altering the specific design presented.

Various flexible hinge and adhesive lap components were then designed into an 11-layered structure that 'pops up' to realize an articulating microsurgical grasper that includes a cable-driven mechanism for grasping actuation (driven by actuating cable 58) and a flexural return spring 54 to passively open the grasper after it has been closed. A prototype of the grasper, with a final weight of 200 mg, overall footprint of 18 mm by 7.5 mm, and features as small as 200 microns, is able to deftly manipulate objects 100 times is own weight at the required scale, thus demonstrating its potential use in microsurgery. The pop-up MEMS fabrication process allows the design and fabrication to be scaled either up or down within the range of the pop-up MEMS manufacturing capabilities.

Small joint surgery, such as surgery conducted in a human wrist or fingers, presents a number of significant challenges due to the limited maneuverable workspace and the presence of many delicate structures that should ordinarily be avoided, including sensitive cartilage surfaces and tendons. Current commercially available small-joint surgical instruments are straight, simple tools without any distal articulation that would allow for greater access and dexterity inside the joint. In addition, the robust electromechanical surgical tools at the sub-mm scales required for these procedures are either impossible or commercially impractical to make with existing manufacturing techniques, such as surface/bulk micromachining, wire-electrical-discharge-machining (wire-EDM), micro-injection molding, or micromilling/lathing. The micro-machining and assembly technique, described herein, enables robust, dexterous, and practical microsurgical instruments for small joint repair.

Figure 3:
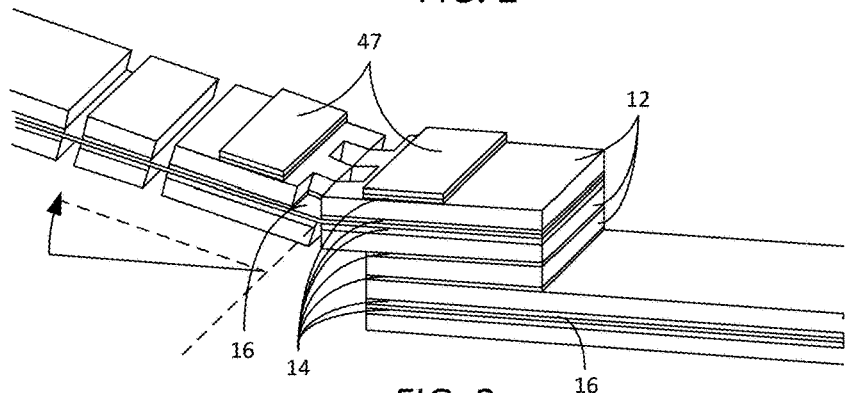
FIG. 3 is an illustration of a layup in the form of a hinge created with pop-up MEMS fabrication technology.

We have developed a micro-manufacturing technique, known as pop-up MEMS ('pop-ups'), that allows for the fabrication of complex, multi-functional electromechanical devices with dimensions on the 0.1-10 mm scale. Pop-up technology enables the ability to create 3-D, multi-material, monolithic meso- and micro-structures using purely 2-D planar manufacturing and origami folding techniques. The method can incorporate techniques from printed circuit (PC) board manufacturing, allowing for the straightforward integration of embedded on-board electronics and power. An exemplary pop-up mechanism, featuring a castellated hinge which allows the top structural layer to fold in on itself to approximate pin joint motion, is shown in FIG. 3, which shows the lay-up detail of a hinge created with the pop-up MEMS fabrication technique. The hinge includes layers of carbon fiber 12, adhesive 14, polyimide film 16 and brass 47.

Figure 4:
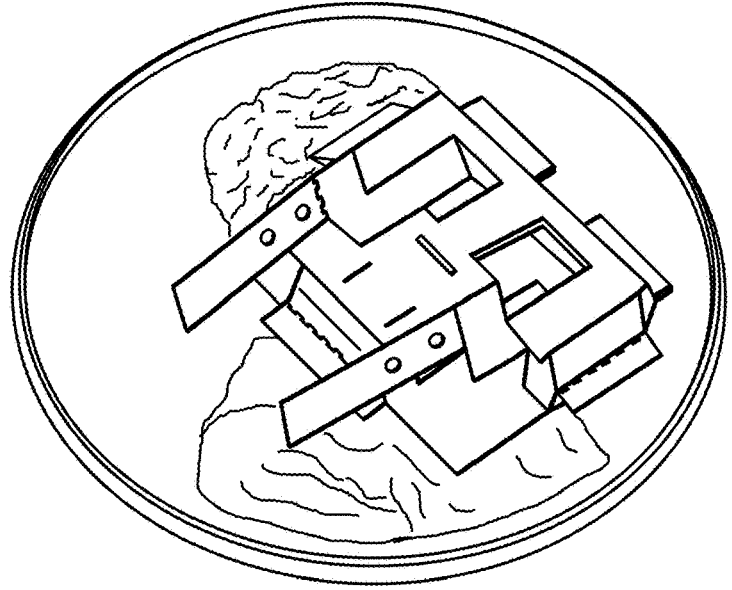
FIG. 4 is a photographic image of a grasper device fabricated using pop-up MEMS fabrication technology on a US penny (0.75 inches in diameter) for an indication of scale.

Pop-up MEMS technology is well-suited for small medical and microsurgical applications, as the technique enables the manufacture of highly capable and articulated mechanisms at sub-mm scales. An early example of a pop-up MEMS grasper device is shown on a US penny for scale in FIG. 4. The nature of pop-up devices enables mechanisms and implants that can be inserted through small incisions and unfold and 'pop-up' to assume their functional form. Embedded sensing and actuation can be directly integrated into the end effector (e.g., jaws 50 in the grasper of FIGS. 6 and 7) to allow for distal actuation and feedback sensing in teleoperative and cooperative robotic scenarios.

To build devices that will mechanically interact with the human anatomy, it is advantageous to understand the forces that these devices can withstand to ensure functional longevity in a mechanically interactive environment. In this section, we begin with an overview of the pop-up MEMS manufacturing process. We provide a discussion of the robustness evaluation experimental methods and present significant results of the evaluation. Finally, we present the design, fabrication, and evaluation of an actuated grasper prototype developed using pop-up MEMS.

1) Pop-Up Fabrication Processes

Mechanisms created with pop-up technology can be composed of a number of layups consisting of five sub-layers, as described above, with a flexible (e.g., polyimide) layer 16 between two rigid structural layers 12 and with adhesive 14 between each of the flexible and rigid layers 16 and 12 (see FIG. 3). The number of layers can scale roughly with device complexity. In this work, 304 Stainless Steel is used as the structural material for the rigid layers 12, and KAPTON polyimide (developed by DuPont) is used as the flexible polyimide layer 16. Dupont FR1500 acrylic adhesive is used as the adhesive 14 to join the layers 12 and 16.

Figure 5:
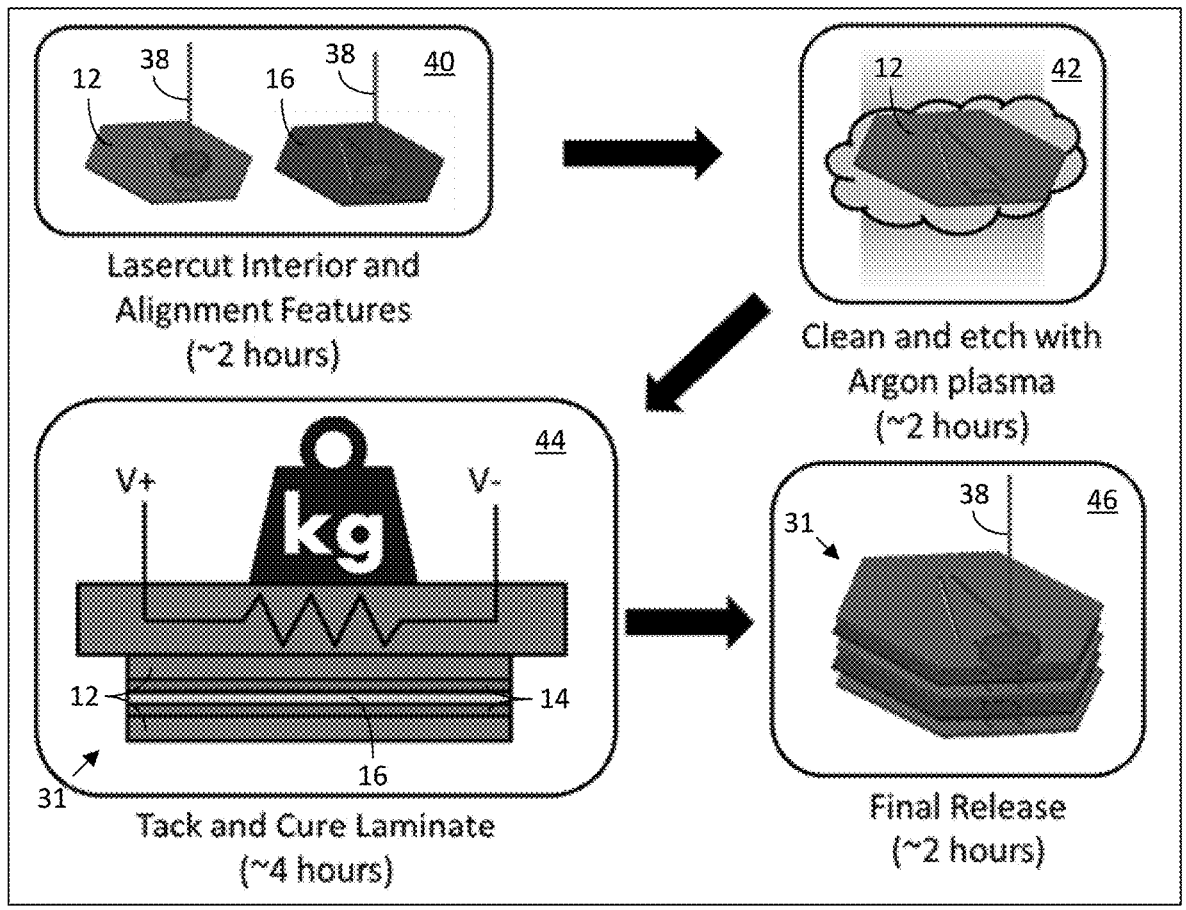
FIG. 5 is a schematic illustration of a pop-up manufacturing process.

An overview of the fabrication process is illustrated in FIG. 5. In step 40, beginning with a two-dimensional (2D) computer-aided-drafting (CAD) model of the device, interior and alignment features on each individual layer 12/16 going into the layup are machined via laser 38 ablation using a diode-pumped solid-state (DPSS) laser. Each layer 12/16 is then deburred, if necessary, and exposed to the following two-step cleaning process in step 42: (1) isopropyl alcohol soak and ultrasonic clean (80° C. for 10 minutes) of each layer to remove surface-level particulates, and (2) plasma etch each layer with argon gas [0.40 mbar at 2-4 standard cubic centimeters per minute (sccm) for 60 seconds] to remove contaminates and to improve the surface microtexture. The layers 12, 14, and 16 are then prepped for lamination and each structural layer is "back-tacked" to deposit the adhesive islands on each respective layer such that the adhesive protective backing can be removed and disposed of. In step 44, the entire laminate 31 is cured via a two-hour curing process where heat (200° C.) and pressure (60 psi) are applied to set the adhesive 14. Following this step, the layup laminate 31 is released from the surrounding alignment scaffold in step 46 using the diode-pumped solid state (DPSS) laser 38 and mechanically "popped up" to assume the functional form of the prototype. From start to finish, the entire fabrication process can take approximately 10 hours.

2) Tool Robustness

Strength and robustness in the design is particularly advantageous for surgical tools manufactured via these principles. Results generated from a robustness evaluation were very extremely encouraging, as pop-up components in the micro-surgical tool were shown to be able to withstand appreciable shear and torsional forces.

Torsional strength of the tool can be increased by providing a curvature radius of 50 μm on the castellation corners of the castellated hinge (as shown in FIG. 3) to prevent the steel castellations from piercing the KAPTON polyimide layer 16, as piercing the KAPTON polyimide layer 16 results in structural failure. Additionally, inclusion of the KAPTON polyimide layer 16 was found to improve layup adhesion and shear resistance; and the quality of adhesion was found to improve proportionably with the amount of KAPTON polyimide present. Though not limited by any particular theory, one reason why the KAPTON polyimide layer may improve adhesion in this context is that exposure to argon plasma improves the surface energy of the KAPTON polyimide, thereby improving its overall adhesive properties. Argon-treated KAPTON polyimide has a larger polar surface energy component (~60 mN/mm) than argon-treated 304 Stainless steel (~50 mN/mm). Since acrylic adhesive is polar by nature, KAPTON polyimide forms a stronger bond with the adhesive 14 than the steel in layer 12, which must rely on weaker dispersive (Van-Der-Waals) bonds.

The shear resistance of the adhesive joint can be approximately as strong as the tensile strength of the steel, itself. Peel failure may be the weakest link, but compensatory design work can be undertaken to ensure that this failure mode never happens in practice, including interlocking structural elements to prevent overextension.

3) Micro-Surgical Grasper

The advent of minimally-invasive surgery (MIS) has cultivated a paradigm shift wherein open surgical procedures can now be performed through a number of small, millimeter-sized ports which can be quickly sutured closed, thus reducing patient morbidity and recovery time. The small scale of these procedures presents significant challenges to developing robust, smart, and dexterous tools for manipulating millimeter and sub-millimeter anatomical structures (e.g., vessels or nerves) and surgical equipment (e.g., sutures or staples).

To meet the demand for next-generation medical end-effectors, the versatile fabrication process, described herein, can be used to create monolithic, kinematically complex, three-dimensional machines in parallel at the millimeter to centimeter scales.

As a demonstration of the feasibility of pop-up MEMS for developing miniature medical devices, the manufacturing process outlined above was used to develop a micro-surgical grasper prototype that includes a plurality of the adhesive lap joints and hinge joints evaluated in the previous section. The prototype was designed with a form-factor (1 mm×10 mm grasper jaws) consistent with microsurgery requirements in an effort to fabricate a grasper for robotic work, e.g., as described in F. Hammond III, R. Kramer, Q Wan, R. Howe and R. Wood, "Soft Tactile Sensors for Micromanipulation," in *Proc. of* 2012 *IEEE Int. Conf. on Intelligent Robotics and Systems*, Vilamoura, Portugal (2012). The grasper was designed with cable-driven actuation for the closing mechanism and with a flexural spring that applies a restoring force to passively open the grasper. Conceptual images of the grasper prototype is shown in FIGS. 6 (top view) and 7 (side view), where the grasper is respectively shown in open and retracted positions.

As shown in FIGS. 6 and 7, the grasper includes two gripper jaws 50, one of which is coupled to a passive restoring element 54 (e.g., a spring) that is coupled at an opposite end with a restoring ground 56. The grasper is shown at rest and in equilibrium in FIG. 6. An actuating cable 58 is coupled with both jaws 50 via a Sarrus linkage 52 in the form of an interior castellated hinge. In this particular embodiment, the actuating cable 58 is coupled with an actuation linkage 62 to form the Sarrus linkage. When the actuating cable 58 is pulled (to the right in the embodiment shown in FIG. 7), the tension in the actuating cable 58 (working in concert with the restoring force provided by the passive restoring element 54) forces together the distal tips of the jaws 50, as shown in FIG. 7, to thereby enable the grasper to grasp an object between the jaws 50.

In designing the grasper with a passive return, a tradeoff exists between grasper closing range-of-motion (spring compliance) and restoring force (spring stiffness); consequently, serpentine springs 25, as shown in FIGS. 8 and 9, were evaluated empirically and analytically for both of these characteristics. The spring 25 is in its resting state when the mechanism is popped open, and deforms out of plane when actuated to provide a restoring force when the actuating force is removed. The complicated behavior of the spring deformation (out-of-plane, as demonstrated in FIGS. 8 and 9) warrants a more rigorous analysis than simple first-principles.

The spring return was designed using a quasi-analytical process with empirical validation. The stiffness characteristics were approximated via an analytical model of serpentine springs 25 (out-of-plane deflection, as in side view of FIG. 9) to obtain order-of-magnitude flexural behaviors.

$\delta_z$ Deformation in z-direction
E Young's modulus of 304 SS steel
F Applied force
G Shear modulus of 304 SS steel (=E/2(1 v)
$I_{y_o}$ Second moment of area
$I_c$ Torsional moment of inertia
$K_{\delta_z}$ Out-of-plane stiffness, z-direction
$l_z$ Minor length
$l_P$ Major length
N Number of turns $$K_{\delta z} \sim \frac{6EI_{y_o}GJ_o}{(N+1)l_o^3 GJ_o + (16N^3 + 36N^2 + 43N + 3)l_P^2 l_o EI_{y_o}} \quad (1)$$

$$\delta_z \sim \frac{F}{K_{\delta z}} \quad (2)$$

Several spring designs were fabricated and characterized empirically in a tensile testing device (from Instron of Norwood, Mass., US) to verify the analytical approximation. Example behaviors of two disparate flexure designs are shown in FIG. 10. The results demonstrate excellent agreement (less than 10% spring constant error in both cases) between the estimated (Eq. 1) and empirical results in the linear region of spring operation. Once the load/displacement curve becomes sufficiently nonlinear (>5% deviation from linear fit), the spring 25 is assumed to have plastically deformed, thus setting an upper-bound on spring range-of-motion and grasper stroke.

The frictional resistance inherent to the castellated hinge joints (due to stiffness of the KAPTON polyimide, the presence of residual adhesive in the vicinity, etc.) was unknown. Consequently, the stiffer spring with the behavior shown in FIG. 10 was employed in the prototype design to provide sufficient restoring force against this hinge frictional component.

4) Micro-Surgical Grasper Design and Fabrication

An exploded CAD model of the grasper prototype, implementing the flexural return spring 54 described above, is shown in FIG. 11. The entire structure consists of 11 layers (sequentially numbered in FIG. 11), with 304 stainless steel sheet stock (51-μm thick) as the rigid structural layer 12 and 25-μm thick KAPTON polyimide film as the flexible layer 16.

Figure 12:
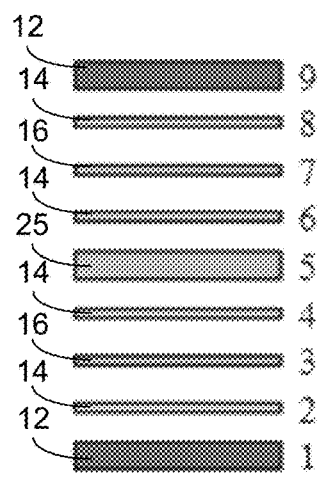
FIGS. 12-14 are illustrations of a spring-actuated pop-up assembly of a micro-surgical grasper.
Figure 13:
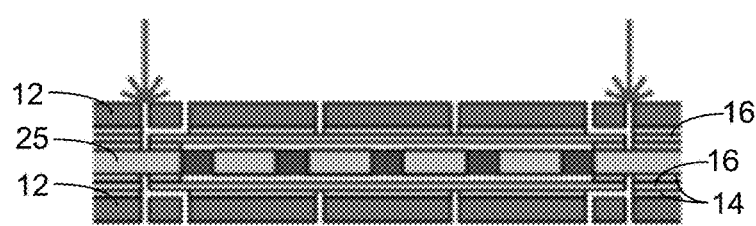
Figure 14:
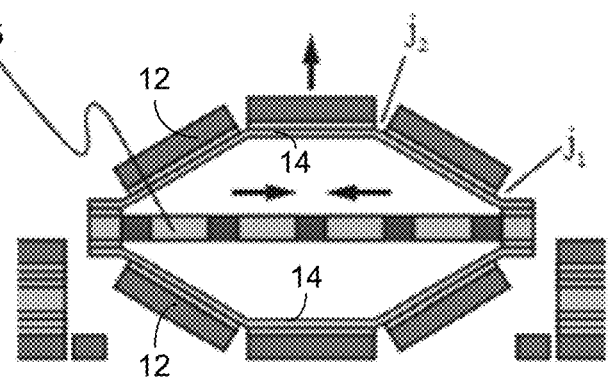

Illustrations of a spring-actuated pop-up assembly of the grasper is shown in FIGS. 12-14, where the grasper is "popped up" by releasing the spring 25 into functioning form. This grasper was fabricated (in one monolithic process) from medical-grade materials and was robust enough to withstand substantial forces.

Figure 15:
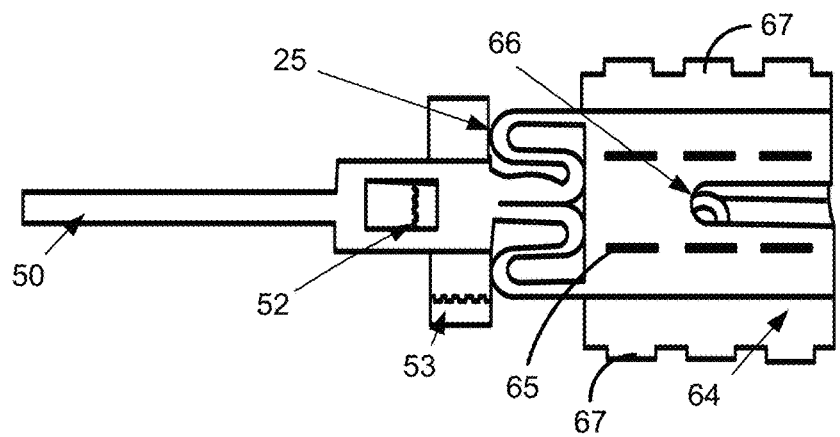
FIG. 15 is a magnified photographic image of an un-popped grasper prototype with labeled features.

The grasper was fabricated using the manufacturing process outlined, above. The manufactured grasper in its "unpopped" (post-release) configuration is shown in FIG. 15. By folding up the notched flaps 64 on the structural end of the grasper (the right half), the tabs 67 on the bottom layer fit into the slots 65 on the top layer, locking the grasper into its fully-assembled (popped-up) configuration. Solder or a contact adhesive can be applied to these interfaces to fix the grasper in this configuration. A drawbeam is machined directly into the bottom layer with an alignment interface for installation of cabling, which when pulled actuates the foremost interior hinge 52 to close the grasper. Two external hinges 53 constrain any transverse movement between upper and lower grasper jaws 50 so that a pure closing motion is achieved.

Figure 16:
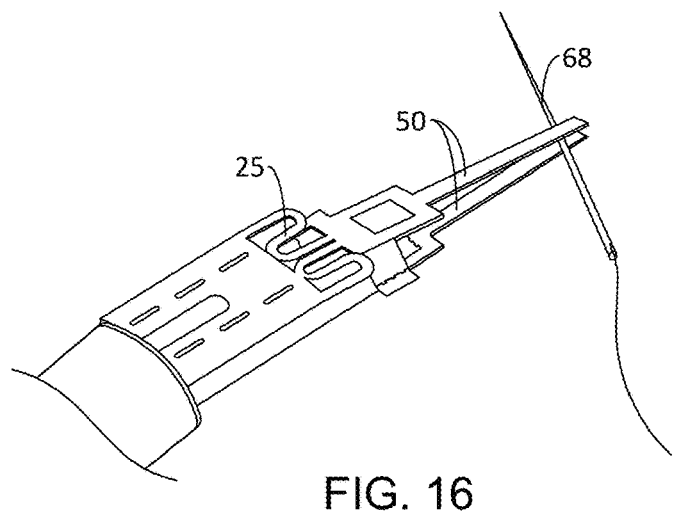
FIG. 16 is a magnified photographic image of a grasper prototype manipulating a suture needle.

An image of the jaws 50 or a "popped-up" grasper manipulating a 19-mm, 1.5-gauge (m) straight-taper suture needle 68 is shown in FIG. 16. The grasper is capable of full closure when actuated by the cable 58 attached to the interior hinge 52 (see FIGS. 6 and 7). As designed, the grasper returns to an "open" position when the actuation load is removed from the cable 58. As can be seen, the stiffness of the spring 54 is large enough such that the grasper approximates an "alligator-jaw" closing motion typical of commercially-available forceps and graspers.

Benchtop tests were performed where the grasper was actuated to grasp and lift sequentially increasing, calibrated weights. The grasper can manipulate steel weights up to 20 g, which is roughly 100 times the grasper's weight of 200 milligrams. The upper limit of the grip force is set by a poor friction interface between the grasper and the object, as well as by the compliance in the grasper jaws 50 given the 10:1 length-to-width aspect ratio.

In additional embodiments, at least one electrode (or an array of electrodes, as described herein) is included in a jaw 50 of the grasper. The electrode(s) is/are coupled with the electrical wiring/traces through the electrically conductive layer to a voltage source and can be used to provide electrocauterization or ablation of tissue during a surgical operation.

5) Strain Gauge Design and Characterization

Figure 17:
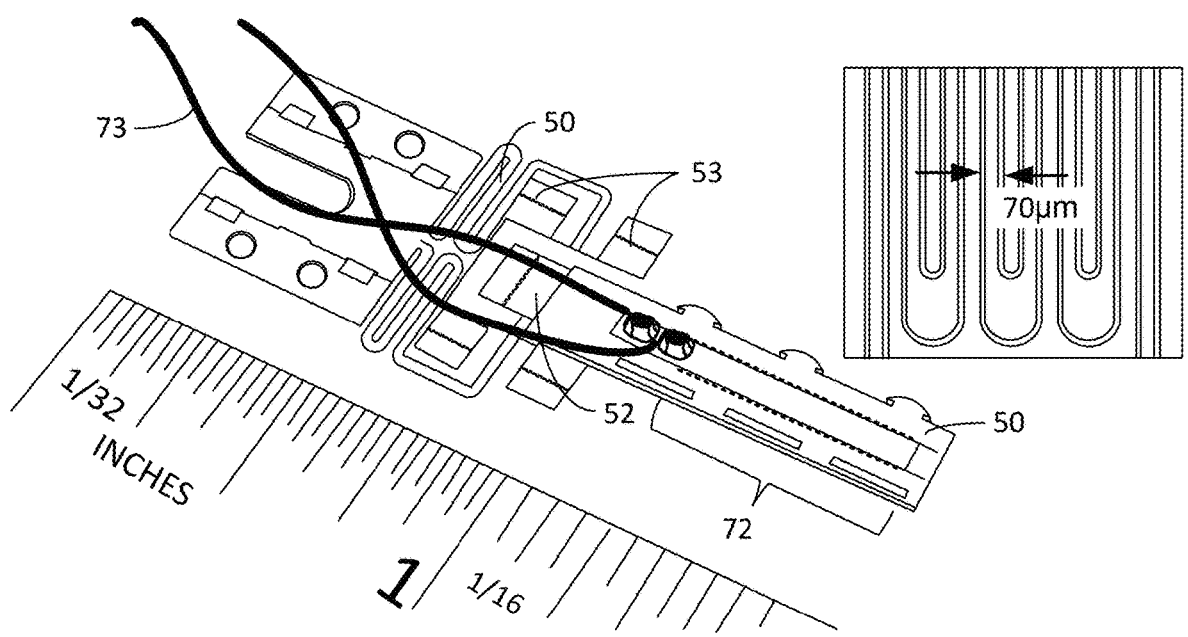
FIG. 17 is a magnified photograph of an integrated micrograsper top layer, unfolded, with a strain gauge embedded in its jaw, alongside a ruler with measurement indicia in inches.

The grasper shown in FIG. 17 includes a strain gauge 72 printed on the jaw 50. The strain gauge 72 can be coupled via electrically conductive wiring 73 (e.g., having an electrical conductivity that is at least half as high as the conductivity of copper) to a voltage detector that detects current generated by deformation of the strain gauge 72. The electrically conductive wiring can alternatively be incorporated as traces in a layer of the laminate structure, as described herein. In this embodiment, the grasper is shown to have a maximum dimension of about 2 inches, though other sizes can likewise be fabricated and used.

Figure 18:
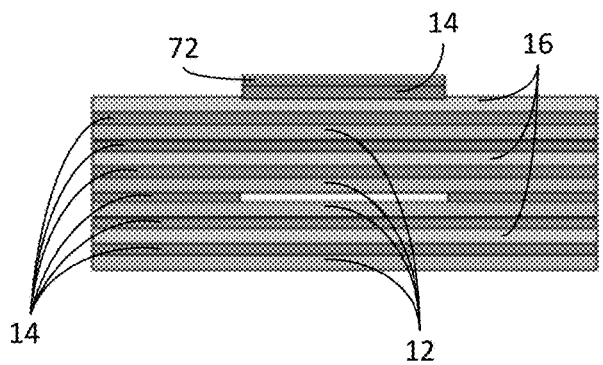
FIG. 18 is a cross-sectional illustration of a pop-up grasper layup with gauge material integrated into the top layer.

A cross-section of the grasper layup is shown in FIG. 18. In this embodiment, the composite layup for the entire grasper consists of 15 layers of alternating structural, adhesive and flexible layers 12, 14, and 16. The layup includes 50 μm-thick 304 stainless steel as the structural layer 12, 25 μm-thick polyimide as the flexible layer 16, and 5 μm-thick gauge material 72 integrated directly into the top layer. The layup is bonded using DuPont FR1500 acrylic sheet adhesive 14.

The strain gauge 72 is designed to detect loads applied to the distal end of at least one of the jaws 50 of the grasper so that force magnitude can be accurately sensed given gauge calibration data and a linear elastic assumption. In an exemplary microsurgery application, where the grasper interacts with mm-scale nerves and vessels, the gauge 72 may be required to sense distal loads up to 1 N with a force resolution of 20 mN. This requirement places an upper-bound on the noise floor of the sensor after signal conditioning.

Figure 19:
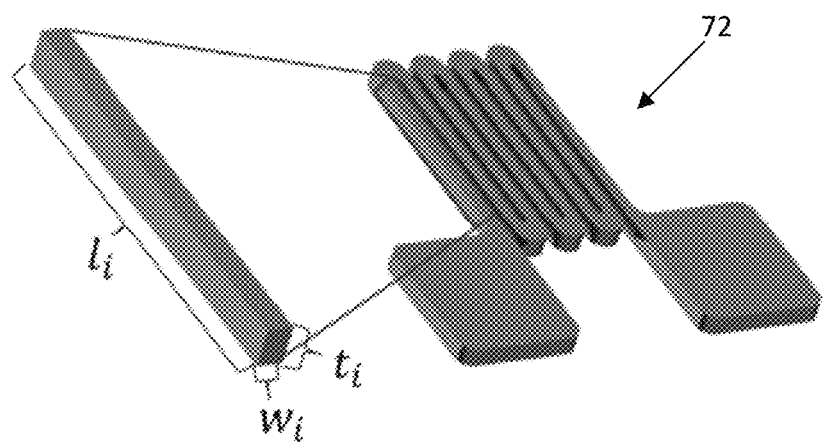
FIG. 19 is a schematic illustration of a discrete element in a complicated gauge pattern.

Given the design requirements set forth in the previous section, the geometry of the gauge pattern can be designed with several considerations in mind. The foremost design challenge is to maximize the gauge factor, $S_e$, while minimizing the overall footprint, where:

$$S_e = \frac{\Delta R_S/R_S}{\varepsilon}, \tag{3}$$

where $R_S$ is the nominal gauge resistance, $\Delta R_S$ is the resistance change induced by mechanical deformation, and $\varepsilon$ is the material strain. Assuming a linear elastic, isotropic gauge material, for a given gauge configuration, we can express the resistance equation, $R = \varrho\, l/A$ as a function of applied strain, $\varepsilon$, to obtain an analytical model for the change in resistance assuming uniaxial loading, as follows:

$$\Delta R_s(\varepsilon) = \rho \sum_{i=1}^{N} \frac{l_i}{w_i t_i}\left(\frac{(1+\varepsilon)}{[(1-\nu\varepsilon)^2]} - 1\right), \tag{4}$$

where $\varrho$ is the resistivity of the gauge material, and $\nu$ is the Poisson ratio. Assuming a complex geometry, we have summed resistance contributions from each discrete feature (length, $l_i$, width, $w_i$, and thickness, $t_i$) of the gauge pattern. FIG. 19 demonstrates the geometry of a discrete element in a more complicated gauge pattern.

From Equation (4), the sensitivity of the gauge 72 is directly proportional to length, $l_i$, and inversely proportional to cross-sectional area, $A_{c,i} = w_i t_i$. Serpentine gauge patterns typical of commercial off-the-shelf (COTS) metal foil gauges are designed to optimize this relationship. For this reason, a serpentine gauge pattern was implemented to fit the form factor of the grasper jaw 50. Other gauge patterns that are sensitive in multiple other directions could also be implemented for sensing other motions besides bending of the jaws 50.

Practical machining considerations, such as the DPSS laser tolerance, thermal conductivity of the gauge material, and potential inclusion of foreign particulates, limit the smallest achievable feature size to around 50 µm. As such, gauge factors (Equation 3) using this process are limited to 1-2 according to Equations (3) and (4).

An additional consideration concerns thermal power dissipation as wasted heat goes towards thermal expansion of the substrate material, which is detrimental to sensor accuracy and long-term stability. Using a lumped impedance model where each material layer separating the gauge material from the steel substrate is assigned a thermal impedance (both conductive and convective, see the equivalent circuit in FIG. 20), steel substrate temperature versus gauge resistance was analytically determined to facilitate selection of gauge nominal resistance:

$$K \cdot \begin{bmatrix} T_{amb} \\ T_g \\ T_{a1} \\ T_k \\ T_{a2} \\ T_{ss} \end{bmatrix} = \begin{bmatrix} Q + K_{g,amb}T_{amb} \\ 0 \\ K_{g,amb}T_{amb} \\ 0 \\ 0 \\ K_{g,amb}T_{amb} \end{bmatrix}, \quad (5)$$

where $Q=(V_{cc})^2/4R_s$ is the heat dissipated across the gauge 72 (assuming a balanced bridge configuration), T is the temperature vector, and K is a 6×6 matrix comprising thermal conductivities of each layer in the laminate through which heat is conducted. Solving this linear system of equations for $T_{ss}$ tells us the temperature at the surface of the steel layer 12.

A theoretical curve of steel substrate temperature 70 versus gauge resistance is shown in FIG. 21. Steady-state temperatures below 30° C. are desirable to minimize deviation from ambient; and as such, a gauge 72 was designed with a nominal resistance of above 200Ω. Ambient temperature 71 is also plotted for comparison.

Given grasper jaw dimensions, the minimum achievable feature size using DPSS laser machining, and thermal considerations, the gauge 72 was designed to have a nominal resistance, $R_s=270\Omega$, with a predicted gauge factor of $S_e=1.4$ using Equations (3) and (4).

Once the gauge pattern was designed, it was integrated directly into the manufacturing of the mechanical grasper structure using pop-up MEMS fabrication. Constantan foil (5 µm thick, 45% Cu, 55% Ni) was chosen as the sensing layer due to its high resistivity (~520×10⁻⁹ Ω/m), versatility, biocompatibility, and comparable thermal expansion (15.0 ppm/° C.) with 304 SS (17.2 ppm/° C.).

The Constantan foil 72 was laminated to the top structural layer 12 of the grasper, as in FIG. 22, which shows a conceptual layup of the top grasper jaw 50. KAPTON polyimide 16 provides an extra layer of insulation between the gauge 72 and the steel substrate 12.

The delicate nature of the thin Constantan foil 72 yields special processing considerations. The strain gauge 72 is machined and laminated in parallel with the mechanical structure, and as a result, the gauge material experiences significant thermal gradients (~200° C.) during lamination. The residual stress, $\sigma_{therm}$, induced on the gauge material during the lamination process can be calculated using a thin-film approximation by assuming the thermal behavior is dominated by the steel substrate 12:

$$\sigma_{therm} = \frac{E_{const}}{(1-v_{const})}(\alpha_{T,const} - \alpha_{T,s})\Delta T, \quad (6)$$

where $E_{const}$ is the Young's Modulus of Constantan (169 GPa), $v_{const}$ is the Poisson ratio (0.33), $\alpha_{T,const}$ is the thermal expansion coefficient for Constantan (15 ppm/° C.), $\alpha_{T,s}$ is the thermal expansion coefficient for 304 SS (17.2 ppm/° C.), and $\Delta T$ is the process temperature gradient. Based on these parameters, the thermal stresses, $\sigma_{therm}$, induced via lamination are on the order of 166 MPa, resulting in a safety factor of about 3 (given $\sigma_y=500$ MPa for Constantan) demonstrating that thermal stressed induced during the manufacturing process will not result in failure.

After the gauge material was laminated directly onto the grasper layup, the serpentine gauge pattern was machined into the Constantan foil during the release step following the full cure. At this point, the foil 72 is already fully bonded to the polyimide insulating layer 16, so the depth of cut is closely controlled such that the insulating layer 16 is not ablated by the laser, providing a conductive path to the steel substrate 12.

Following successful manufacture of the gauge material integrated to the structural substrate, the gauge forms one leg of a Wheatstone bridge with tunable balance to account for gauge manufacturing variations. The output of the bridge is amplified via a differential operational amplifier (LM741CN) with a gain of 500. Data is then acquired via an Analog-to-Digital Converter (ADC) and passed to the host PC through a serial interface at a sampling rate of 500 Hz. Assuming a perfectly balanced bridge, the relationship between gauge resistance change and output voltage is given by Equation (7).

$$\Delta V_{out} = GV_{cc}\left[\frac{R_s}{2R_s + \Delta R_s} - \frac{1}{2}\right]. \quad (7)$$

This amplification circuit boosts fractional gauge resistance changes to measurable voltages such that strains are resolved with much higher resolution.

Using the manufacturing process outlined, above, sample gauges 72 were manufactured onto 5 mm by 30 mm 304SS beam substrates with 100 µm thickness for gauge characterization. The simple geometry allows for a more straightforward strain characterization based on linear elastic principles.

The average nominal resistance of the manufactured gauges is 278±7.16Ω (95% confidence for 6 samples), which is close to the design resistance of 270Ω computed using Equation (4). The steady-state operating temperature, measured using a thermocouple and data logger, was measured to be approximately 6.5° C. above ambient, which agrees with the predicted value of 6.85° C. obtained via thermal impedance modeling, Equation (5).

Two tests were performed to validate gauge performance. For the first test, gauges 72 were secured to a benchtop in a cantilever fashion, and discrete weights of known mass were hung on the distal end of the gauge 72. The resulting change in voltage was recorded, and $\Delta R_s$ was solved for using Equation (7). The strain was calculated as follows:

$$\varepsilon = \frac{mgcL}{E_s l}, \quad (8)$$

where m is the load mass, g is the universal gravitation constant, c is the distance separating the location of the maximum stress (at the gauge surface) from the neutral axis of the beam, L is the length along the beam where the load is hung, $E_s$ is the Young's modulus of 304 SS, and l is the second moment of area.

The second characterization approach was experimentally more rigorous but enables an even simpler model to compute strain. Using an Instron tensile testing machine with a static load cell, gauge samples were loaded in uniaxial tension over a triangular force profile (4 N/s) up to approximately 50% of $\sigma_y$, corresponding to a maximum tensile load of 200N. Data were collected at a rate of 500 Hz and post-processed in MATLAB. In the case of composite uniaxial tension, and accounting for elasticity in the polyimide layer, the strain is computed as:

$$\varepsilon = \frac{F}{(A_k E_k + A_s E_s)}, \quad (9)$$

where $A_k$, $A_s$, $E_k$, and $E_s$ denote cross-sectional areas and Young's moduli for polyimide and 304SS, respectively. The adhesive layers are assumed to not contribute significantly to the deformation of the substrate.

Results of the tests showed that both methods yield consistent results. The measured gauge factor is 1.1, which is a typical number for thin metal foil gauges.

In addition to mechanical characterization, the thermal characteristics of the gauge are adequately determined to quantify stability of the sensing system when operating in environments with varying temperatures. The thermal expansion of the steel structural material induces strain in the gauge material, resulting in resistance drifts as a function of temperature. Recalling Equation (2), and replacing mechanical strain with thermal strain ($\varepsilon_{therm} = \alpha \Delta T$), the change in resistance due to temperature gradients can be computed via the following equation:

$$\Delta R_s(\Delta T) = \rho \sum_{i=1}^{N} \frac{l_i}{w_i t_i} \left( \frac{(1+\alpha\Delta T)}{[(1-v\alpha\Delta T)^2]} - 1 \right). \quad (10)$$

Experimental data was collected to compare to the analytical model described by Equation (10). Gauges were heated on a hot plate; instantaneous temperature was recorded with a thermocouple and datalogger; and the resistance was recorded using a digital ohmmeter. The sensors demonstrated a sensitivity of 7.1 mΩ/° C. Plugging into Equation (7), the voltage sensitivity is G·31.7 µV/° C., where G is the differential gain. In an anatomical setting, temperature gradients of up to 15° C. can be expected, resulting in a voltage swing of over 200 mV for 500 gain. Therefore, inclusion of a temperature-compensating gauge is advantageous.

To demonstrate the efficacy of embedded strain sensing in an integrated platform, a 2:1 scale minimally invasive surgery (MIS) end effector with the strain gauge 72 directly integrated was fabricated using the pop-up manufacturing process outlined above. The gauge 72 was fabricated in parallel using the same process, yielding a fully-integrated force-sensing end effector with no post-manufacturing bonding, alignment or gauge assembly required.

The mechanical design of the grasper is improved structurally by incorporating three-dimensional features that fold out of plane and lock into place to increase jaw stiffness over a planar jaw with no out-of-plane features (see illustration in FIGS. 23-25). If we consider bending about the x-axis as defined in FIG. 23, we can compute the second moment-of-area, $J_{xx}$, of the folded-over jaw 72 as follows:

$$J_{xx} = \frac{bh^3}{12} - \frac{(b-2t)(h-2t)^3}{12}, \quad (11)$$

where b and h are width and height, respectively, as shown in FIG. 25; and t is the thickness of the laminate. Comparing to a 2D planar jaw where $J_{xx} = bt^3/12$, the stiffness is improved by over 200 times given b=2 mm, h=1 mm and t=150 µm. A flexural return spring 54 is placed in line with the actuation force from the cable 58, and is designed to remain elastic over the 4 mm range of motion that comprises the grasper's overall travel while providing sufficient restoring force to overcome gravity and hinge friction. The result is a pure parallel closing motion, with castellated hinges acting as rotary bearings to constrain any transverse motion. Previous studies have shown these castellated hinges to resist torsional loads of 22.8±2.15 N·mm per mm of hinge width, and given four 3 mm wide hinges, the grasper is expected to endure maximum tip loads of around 4 N which provides a significant factor-of-safety over the design load of 1 N.

Figure 26:
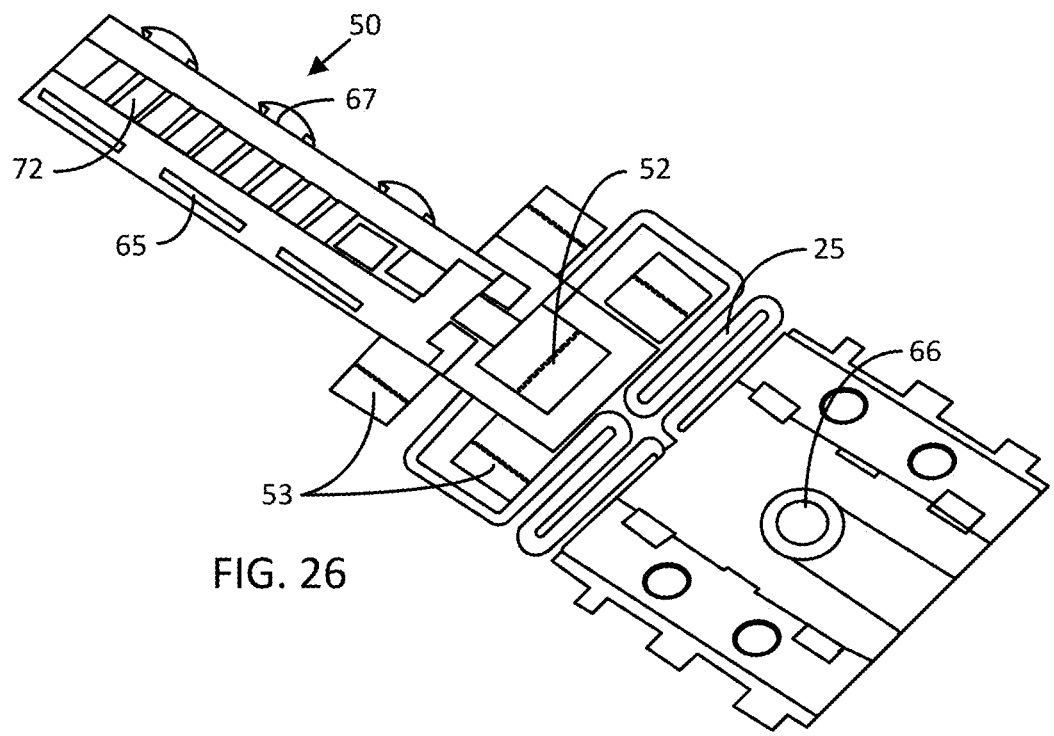
FIGS. 26 and 27 are images of force sensing micrograspers—post-release cut and unpopped (FIG. 26) and popped up with the top jaw folder over to insulate the gauge (FIG. 27).

The gauge 72 is completely enveloped by the fold-over jaw design, which serves to both physically isolate the gauge 72 from the environment and to provide protection against stray capacitance via the Faraday Cage effect. Additional insulation can be provided by potting the gauge area with an epoxy. Solder pads are encompassed entirely inside the foldable jaw 50, so there are no exposed leads. The stiffness of the jaws 50 is substantially higher than that of the sample beams used for gauge characterization, so the gain of the amplifier circuit was increased from 500 to 1650. RMS noise from the circuit is on the order of 15 mV. Images of the integrated grasper, both post-release ("unpopped") state and partially popped with the jaw 50 folded over to insulate the gauge 72, are shown in FIGS. 26 and 27.

The static performance of the integrated grasper was evaluated in a similar manner as the standalone gauge. From the characterization data, the sensitivity followed a linear trend of approximately 458 mV/N. Considering the RMS noise of 15 mV caused by the high-gain differential amplifier, the strain gauge 72 can detect loads of upwards of 33 mN, which is very close to the design target of 20 mN resolution.

Figure 28:
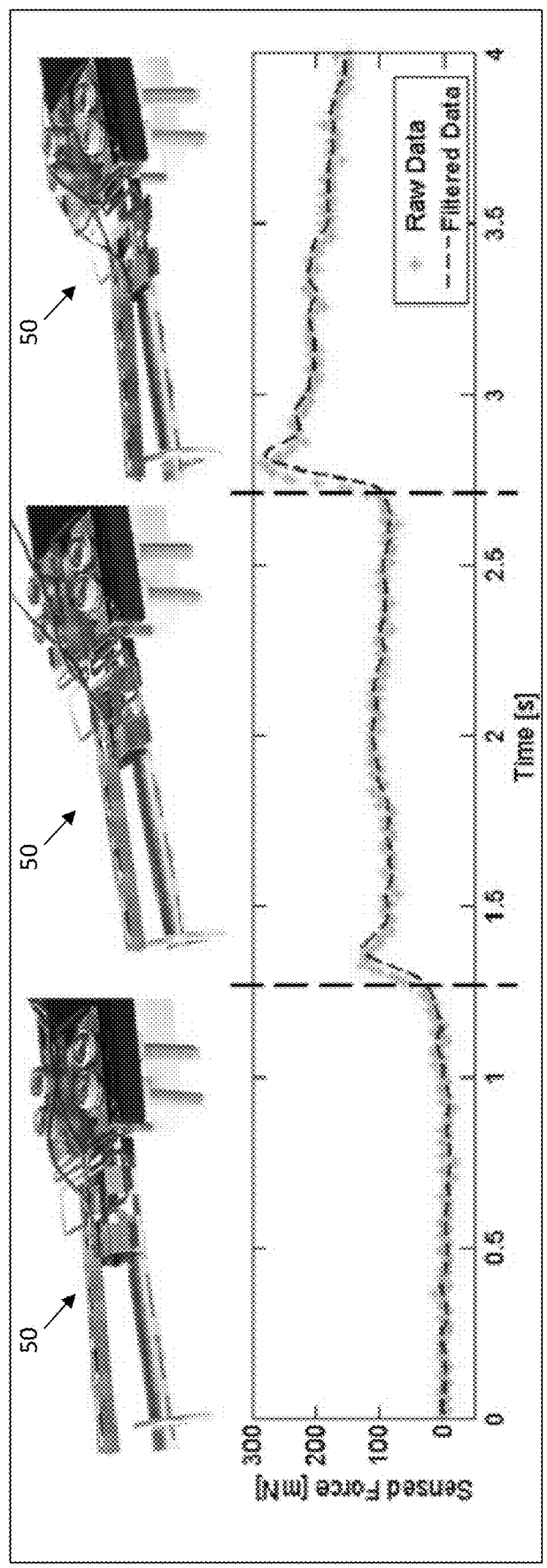
FIG. 28 plots the measurements of a strain gauge integrated on a jaw of a micro-grasper in an unloaded state (left)

FIG. 28 shows images of the grasper 50 undergoing a simulated manipulation task, along with the force signals (raw data and filtered via 2nd-order Butterworth filter) generated throughout the task. The grasper was able to distinguish between states of no-load, initial contact or light-load, and heavy-load. The overshoot at each loading phase is due to the deformation of the flexural return spring 54, which, in addition to providing mechanical damping in the system, initiates a second-order response.

In additional embodiments, micron-feature-sized strain gauges 72 are produced directly on surfaces associated with assembled robotic systems or subsystems. This method provides for application of the gauge 72 to both in-plane (flat) and out-of-plane (curved) surfaces. Surfaces are prepared with a preliminary 35 μm-thick layer of parylene C (p-xylylene polymer). A micron-feature-sized polyimide (KAPTON) mask 60 μm in thickness is prepared using a DPSS laser system and applied to the test surface allowing direct sputtering of the strain gauge material using, e.g., the Denton Vacuum Desktop Pro confocal sputter deposition system. Copper strain gauge bond pads are also sputtered onto the component surface, and electrical connections are established. A final 35 μm-thick coating of parylene C is then deposited to create the composite strain gauge in place.

Nichrome strain gauge traces on the order of 75 μm wide, 150 nm thick and 10 mm in length were tested on a metallic tubular robot, and small strain (0.2%) gauge factors were found to be on the order of G=4.9. Similar testing on carbon fiber composite material yields similar results. This same process can be used to produce other sensors—e.g., along one or more of the grasper jaws for measuring contact location or pressure or for measuring axial force. In additional embodiments, other types of sensors (e.g., a thermocouple for sensing temperature) can be included among the layers in addition to or an alternative to the strain sensor.

6) Supplemental Exemplification of Grasper

The mechanical actuation of a grasper is shown in FIG. 29. All motion is permitted by flexure-based kinematics, using KAPTON polyimide as the flexure layer. Two jaws 50 are brought together by pulling at the midpoint of an internal Sarrus linkage 52. An in-plane steel serpentine flexure 25 deforms upon actuation, thus providing a restoring force that passively opens the grasper once the actuation force is removed. This flexure 25 also supplies a counter-torque about the Sarrus linkage 52 to close the jaws 50 in a 'pinching' motion. The closure kinematics can be arbitrarily selected by adjusting the distance between the flexure attachment point and the location of the internal Sarrus linkage 52. Two external linkages 53 (one on each side of the grasper) act as rotary bearings to constrain any transverse motion between the jaws 50.

The sensor 72 is a custom-designed serpentine-style strain gauge that resembles commercial off-the-shelf (COTS) thin-film strain gauges. In order to achieve thermal stability, a half-bridge is completed on the structure of the gripper, itself, such that the force-sensitive gauge 72 is biased by an identical gauge placed in a location that experiences no mechanical loading, but experiences the same thermal expansion. Thus, the geometric footprint of the sensor 72 is constrained so that two gauges can be placed on the grasper surface. Analytical modeling was used to design a gauge with a footprint of 1 mm×3 mm and a nominal gage resistance of 120Ω.

The grasper was manufactured using the pop-up MEMS fabrication process, described herein. During lamination, precisely aligned material layers were combined in different ways to create functional layers that serve a specific purpose. The combined layers included structural layers, flexure layers that enable rotary joints and articulated structures, printed circuit board (PCB) layers, electrically insulating layers, adhesive layers, or metal spring layers. Finally, various functional layers were combined to create multi-structure, multi-material, quasi-2D laminates capable of folding into complex 3D structures.

An exploded view of the layer-by-layer composite manufacturing of the top layer of a gripper, incorporating a structural sub-laminate 80, a sensing sub-laminate 82, and an encapsulation sub-laminate 84 is shown in FIG. 30. 304 stainless steel was chosen as the structural layer 12, with KAPTON polyimide acting as the flexible layer 16, which enables kinematic motion. Constantan (45% Cu/55% Ni) was chosen as the sensing layer 72, as its thermal expansion properties are very similar to 304 stainless steel. Subsequent layers were joined using PYRALUX FR1500 sheet adhesive (duPont) 14.

After release cuts are made and the grasper is "popped-up", the entire structure can then be coated in a 30 μm thick layer of Parylene which makes the device completely biocompatible. The integrated force-sensing grasper is shown in FIG. 31, where the grasper is shown (middle) post-release (flat) and (right) "popped-up" with a US penny provided for scale.

A custom-designed flexible circuit featuring a manually tunable Wheatstone bridge with adjustable gain (set at 500 for this application) was fabricated, along with a serpentine flexible circuit with traces to connect the gripper to the signal conditioning circuit via a Molex connector. The full implementation (including gripper, wiring, and signal conditioning) is shown in FIG. 32.

The sensor 72 was calibrated by hanging discrete weights of known mass from the distal end of the grasper jaw 50 and recording the resulting voltage. The sensor sensitivity was found to be roughly 4.8 V/N. The root mean square (RMS) noise of the sensor 72, measured by numerically integrating the power spectral density of a null signal measured over one minute, is roughly 23 mV (corresponding to a force of 5 mN).

A demonstration platform was built wherein the grasper is actuated by a trigger, and a real-time force reading is displayed by a light-emitting diode (LED) bar graph, where each bar represents 10 mN of force. This platform is shown in FIG. 33. In addition, force data is output to a serial port via an Arduino Nano microcontroller at a sample rate of 50 Hz for real-time 10-bit analog force display and data post-processing.

To demonstrate the efficacy of the device in an anatomical scenario, a simulated task was performed wherein the grasper manipulated a 19-mm long, 1.5-gauge (m) straight-taper suture needle and drove it through a block of Ecoflex-0010 (Smooth-On), which acts as a tissue analog. The resulting force profile generated from this task peaked at around 80 mN for the grip force and at around 150 mN for the drive force; and the results show that the force sensor 72 was able to detect distal forces with high resolution (i.e., with a resolution of 5 mN) and a sensitivity of 4.8 V/N; and the differentiation between null force, grasping force and driving force was evident.

7) Contributions and Implications

In this section, we have established the utility of pop-up MEMS fabrication for the development of medical devices by demonstrating that these devices can tolerate significant forces before failure, including joint shear stresses of 26.8±0.53 N/mm$^2$ and hinge torques of 22.8±2.15 N*mm per mm of hinge width. Failure behaviors were shown to be very predictable with no incidence of statistical outliers. Strength quantities determined from this evaluation will be used to create scaling laws to aid in the design of future pop-up microdevices.

In addition to the robustness evaluation, we designed and fabricated a grasper prototype with active cable-driven clamping and passive flexure-driven opening. The grasper operated as designed and was able to manipulate objects 100 times its own weight, further demonstrating the value of the pop-up fabrication process for microsurgical instrument development. Successful demonstration of this device provides a springboard for future medical device development using pop-up MEMS.

In additional embodiments, the tool can be manufactured from biocompatible composite materials; surface features may be directly machined into the jaws; high-friction rubber coatings may be provided on the jaw surfaces; jaw stiffness features may be embedded in the jaw to improve clamping performance; and the grasper can be outfitted with additional sensors to measure force and other physiological signals and can be designed for integration (e.g., communication and control) with a robotic system to realize a force-feedback teleoperative surgical system.

Furthermore, we have presented a novel surgical grasper prototype with embedded strain sensing, fabricated entirely using a one-step pop-up MEMS manufacturing approach. The grasper was experimentally shown to detect distal loads as low as 30 mN, with a sensitivity of 408 mV/N. Simple manipulation tasks show that the grasper can reliably differentiate between different loading conditions. We envision a large number of applications for this technology in minimally invasive surgical procedures, including microsurgery and small-joint arthroscopy.

Integrating multiple sensing modalities with miniature mechanical end effectors offers the potential to create smart surgical tools that provide physicians with information that enables them to perform more effective and safe procedures.

Additionally, a surgical grasper prototype with embedded strain sensing, fabricated entirely using a one-step composite lamination manufacturing approach, was experimentally shown to detect distal loads with a resolution of 5 mN and a sensitivity of 4.8 V/N. Simple manipulation tasks show that the grasper can reliably differentiate between different loading conditions.

Deployable Electrode Array

Three layers that are laminated to form an embodiment of an electrode panel are shown in FIG. 65, alongside a ruler with numbered centimeter designations for scale. The first layer 100 is a copper layer that provides electrical circuit connections with the electrodes 180 that will subsequently be laminated thereto. The first layer is here shown with laser-machined electrodes 180, which are applied with the third layer 196, discussed below. The second layer 198 is a KAPTON polyimide layer that serves as a mask with small apertures through which conductive epoxy is flowed to provide a conductive link between the underlying copper layer 100 and the electrodes 180. The third layer 196 is a stainless steel electrode layer with adhesive tape (e.g., GEL-PAK adhesive tape from Gel-Pak of Hayward, Calif.) on its back side. The surrounding scaffold of the third layer 196 is removed, leaving behind the electrodes 180 on copper layer 100. Alternatively, the electrodes 180 can be deposited onto the underlying layers by electroplating or other type of deposition.

A photographic image of a flex circuit layer upon which the electrodes will be mounted to form an electrode panel is provided at the top of FIG. 66. A magnified view of the encircled section is provided at the bottom of FIG. 66, showing the electrical traces 81 printed on the KAPTON polyimide layer 198 in greater detail. The KAPTON polyimide layer 198 is part of a laminate structure with an underlying copper layer and an adhesive layer between the copper layer and the polyimide layer 198. Also illustrated are a plurality of apertures 22 through which dowel pins 20 are passed for alignment during lamination. The electrical traces 81 lead from a voltage source to electrode pads 118 to which the electrodes are electrically coupled.

Images of flexible electrical wiring and traces embedded in the deployable electrode structure are shown in FIGS. 67 and 68. As shown therein, beneath a stainless steel layer 196 with flexible hinges 114, electrical traces 81 (formed, e.g. of copper) and an underlying conductive copper layer 100 traverse across hinges 84 and through mechanical components to allow the electrodes 180 to receive signals without the need for external electrical wiring.

An image of an embodiment of a full, expanded electrode array 79 is provided in FIG. 69, wherein the array 79 includes a plurality of interconnected electrode panels, each with an electrode 180 on its outer surface, and with hinged side plates 90, a steering finger 93.

Integration of Magnetic Actuators in a Layered Fabrication Process

1) Introduction

A generalized process flow for pop-up MEMS fabrication that can be used for fabrication of devices described in this section (and in other sections of this disclosure) is illustrated in FIG. 34. The integration of compact actuators into such a process greatly increases its potential in biomedical, microrobotic, optical, and other applications.

The process commences with lithography 102, as used in printed circuit board processing, wherein selected regions of a photosensitive polymer is exposed to light, and either the exposed or unexposed regions are then selectively removed via etching to form a desired pattern in the polymer coating. Laser machining 40' can optionally be employed to cut patterns in the individual layers.

The layers can optionally be aligned in a layup via alignment 104 on pins. Low-profile components can be positioned via a pick-and-place process 106' on the layup before lamination; and the laminate can then be press cured 44 (under increased temperature and pressure). A second laser machining step 40" can then optionally be employed to release an assembly degree of freedom. This sequence of steps 104-106'-44-40" can be iteratively repeated in certain processes, where desired.

A solder past stencil is the applied to the laminate to serve as a stencil for applying solder paste 108 in processes that incorporate reflow. Components that are not suitable for lamination (e.g., that may be damaged by the heat and pressure in the press cure step 44) are then applied via a second pick-and-place process 106". The device can then be pop-up assembled 110; and pick-and-place assembly 106" can then be repeated to add additional components after pop-up folding.

In a locking step 112, metallic contact pads on the device can be coated via, e.g., a solder bath, solder paste reflow or glue application to fix the popped-up configuration of the device. Finally, the device (and its remaining degrees of freedom can be released 46 from the surrounding scaffold via laser machining.

2) Voice Coil Actuators

Voice coil actuators (VCAs) can be used in many positioning applications (e.g., for lateral positioning of hard drive heads and for vertical positioning of the focusing lens in CD and DVD drives). Compared to piezoelectric actuators, VCAs offer low forces, high displacements, and simple drive electronics, making them an attractive counterpart to piezoelectric actuators for pop-up MEMS designs. However, VCAs are typically assembled using conventional manufacturing processes, which increases the difficulty and cost of integrating them into pop-up MEMS mechanisms.

In this section, several methods are presented for integrating magnetic actuators into pop-up MEMS and similar processes that include lamination and folding of relatively flat material layers. The designs include linear voice coil actuators, rotary voice coil actuators, and simple magnetic actuators consisting of a coil and rotating magnet. These methods are uniquely suited for layered fabrication processes and enable very lightweight and/or low-profile electromagnetic actuators.

VCAs comprise a permanent magnet and a ferromagnetic core arranged in such a way as to create a region of strong magnetic field in an air gap in a particular area of the device. A magnetic coil is positioned in this air gap; when current is passed through the magnetic coil (from a voltage source coupled with the magnet coil via electrically conductive wiring), the coil experiences a force perpendicular to the magnetic field and the direction of the current. VCAs harness this force by connecting a load either to the coil or to the magnetic core (the actuators described here, and the majority of VCA designs, work by attaching the load to the coil).

FIG. 35 shows the basic individual components of a low-profile VCA implemented in pop-up MEMS and suitable for fabrication based on the lamination and folding techniques described in preceding section. As shown the VCA, includes the following components: an outer magnetic core 114, which is a pick-and-place component fabricated by stamping and including a permanent magnet 116; a magnetic coil 118 fabricated as a laminated component; an inner magnetic core 120, which is also fabricated as a laminated component; a multi-layer laminate 122, which is the principal structure enabling pop-up fabrication; and a coil-restraint mechanism 124 fabricated by the pop-up fabrication methods described herein and serving to constrain motion of the coil 118.

The assembled VCA laminate structure 126 is shown in FIG. 36. Pop-up MEMS structures are fabricated as multi-layer laminates that incorporate rigid, flexible, conductive, adhesive, and other layers. As described previously, these layers are combined to create a flat structure that includes rigid links and flexures and may be unfolded, similar to a pop-up book, into a complex 3-dimensional mechanism.

In FIGS. 35 and 36, the multi-layer laminate 122 serves as the mechanical ground and primary substrate for the VCA. The magnetic coil 118 is fabricated from several material layers during the lamination process (pin alignment 104 and press cure 44 process steps in FIG. 34). During this process, the inner magnetic core 120 is also coupled to the load—a pop-up MEMS mechanism. The inner magnetic core 120 is also positioned in the pop-up MEMS layup during lamination (pick and place I process step 106' in FIG. 34).

The assembly comprising the permanent magnet 116 and outer magnetic core 114 is fabricated in a separate step using conventional machining techniques (e.g., stamping, adhesives) and attached to the rest of the VCA components after the lamination process is complete (pick and place II process step 106' in FIG. 34). To ensure that the coil will travel in a smooth and constrained fashion along the inner magnetic core 120, the coil constraint mechanism 124 may be incorporated into the pop-up MEMS laminate. The coil constraint mechanism 124 is a mechanical linkage that limits the orientation and motion of the coil 118, causing the coil 118 to follow a desired trajectory during actuation and minimizing friction against the inner magnetic core 120. Like any pop-up MEMS mechanism, it is initially flat and unfolds during the pop-up assembly process step 110 in FIG. 34. In particular pop-up MEMS designs, the coil constraint mechanism 124 may be incorporated into the mechanical design of the load itself, rather than being a discrete mechanism, as in FIG. 35.

The components in FIGS. 35 and 36 may be used to realize both linear VCAs (FIG. 37) and rotary VCAs (FIG. 38), which are illustrated without showing the outer magnetic core 114. The two arrangements differ in the shape of the coil 118 and magnetic cores 120 and also in the design of the coil constraint mechanism 124. Linear VCAs have a rectangular magnetic core 120 and coil 118 geometry, and the constraint mechanism 124 is designed to enforce linear motion (for example, a set of Sarrus linkages is shown in FIGS. 36 and 37). In rotary VCAs, as shown in FIG. 38, the core 120 and coil 118 are curved along some radius to generate rotary motion, while the constraint mechanism 124 is designed to produce the same rotary motion (FIG. 38 shows a simple beam attached to a vertical flexure at the center of rotation defined by the VCA curvature).

The outer magnetic core 114 is used to channel the magnetic field generated by the magnet 116 and concentrate it in the air gap where the coil 118 resides. FIGS. 39-44 show several possible outer magnetic core 114 shapes and permanent magnet 116 arrangements that enable a compact, low-profile VCA. The magnet 116 and core 114 can be arranged in such a way as to expose either the top, bottom, or both top and bottom surfaces of the coil 118 to a strong magnetic field. Placing only one surface of the coil 118 in the region of strong magnetic field allows for a more compact and lightweight actuator. However, using additional magnets 116 to generate a magnetic field on two surfaces of the coil 118 allows the actuator to generate more force (e.g., the symmetrical arrangements shown in FIGS. 42-44 would generate approximately twice the force of the one-sided arrangements shown in FIGS. 39-41 assuming identical magnets and core dimensions).

In conventional VCAs, the coil 118 is typically fabricated by winding magnet wire around a bobbin structure. To maximize compatibility with layered fabrication processes, it is advantageous to fabricate the magnetic coil 118 by arranging and laminating flat material layers so that the coil 118 may be manufactured concurrently with other pop-up MEMS components. FIGS. 45-50 show two methods of fabricating the coil 118 during lamination, using plated vias 132 (FIGS. 45-47) and using folding (FIGS. 48-50). In both cases, the coil 118 is formed out of two copper-laminated polymer (e.g., KAPTON polyimide) layers 128 patterned using standard circuit lithography. When overlapped and connected mechanically and electrically, the two layers 128 form a single winding.

In the plated via method (FIGS. 45-47), the coil halves 128 are bonded during lamination (FIG. 46) to a low-friction plastic spacer 130 of roughly the same thickness as the inner magnetic core 120. The plastic spacer 130 contains vertical vias where the coil halves 128 are connected electrically; these vias may be formed by laser machining, similar to pop-up MEMS mechanisms, or by conventional drilling. The sidewalls of the vias are coated in a conductive material by physical or chemical vapor deposition followed by electroplating to form the plated vias 132, similar to printed circuit board vias. After bonding, the electrical connections are completed by solder paste reflow or solder immersion (FIG. 47).

In the folding method (FIGS. 48-50), the coil halves 128 are folded around the low-friction plastic spacer 130 during lamination (FIG. 49) using a precision jig. The coil halves 128 are bonded to the plastic spacer 130 and to each other; the coil halves 128 also include an additional polymer layer to insulate the coil 118 electrically from the inner magnetic core 120. After lamination, the coil halves 128 are connected together by solder paste reflow or solder immersion (FIG. 50).

In both methods, the constituent layers incorporate sacrificial features to allow pin alignment, similar to other pop-up MEMS mechanisms. The sacrificial features are cut away and removed after lamination (laser machining II process step 40" in FIG. 34). FIGS. 51 and 52 show a magnetic coil 118 fabricated by the folding method before and after the removal of sacrificial features. Either or both of the plated via method and the folding method may be used to realize coils 118 with multiple layers 128 of wiring. Fabrication of each new layer of wiring 128 includes the layup and lamination steps of FIGS. 45 and 46 (or of FIGS. 48 and 49) repeated with additional patterned copper layers and low-friction spacers 130 on the outside of the existing structure.

Furthermore, FIGS. 53 and 54 respectively show a fabrication process schematic and a physical prototype of a linear VCA with a Sarrus-linkage-based suspension mechanism. In FIG. 53, magnified cross-sectional views of the VCA from planes orthogonal to the page in the corresponding exploded views to the left side of the drawing. As shown, the VCA is formed by curing the adhesive layers 14 and reflowing the coil connections in a single lamination step and then employing the pop-up assembly techniques described herein to expand the laminate device in a third dimension.

FIG. 55 shows the inner magnetic core 120, magnetic coil 118, outer magnetic core 114, and permanent magnet 116 of an assembled VCA. Any (or all) of the copper-laminated polymer layers 128 used to form the magnetic coil 118 can extend into the pop-up MEMS laminate and be patterned appropriately to be used as a printed circuit board to house drive and control electronics associated with the VCAs. The board may be populated at the same time that other pick-and-place components, such as the outer magnetic core 114, are delivered.

3) Simple Rotary Actuator

A simple electromagnetic actuator, shown in FIGS. 56 and 58, may be realized by positioning a permanent magnet 116, constrained to pivot around its axis, inside a coil 118. By passing current (from a voltage source electrically coupled with the coil 118) in either direction through the coil 118, a magnetic field is created—essentially, an air-core electromagnet. The opposite poles of the electromagnet and the permanent magnet 116 attract, producing a torque on the magnet 116. An arm may then be attached to the permanent magnet 116, allowing it to drive a useful load. While this type of actuator has lower power density compared to a voice coil, it can be used as a simple and convenient way to implement rotary motion.

Miniature actuators of this type are used routinely in hobbyist aircraft to move control surfaces. These are custom designed actuators, frequently assembled by hand and requiring a high level of craftsmanship. The folding mechanisms of pop-up MEMS can be used to mass-produce such actuators in a much more precise and repeatable manner, offering the potential for increased miniaturization, cost reduction, and complex mechanical designs with large numbers of actuators driving different degrees of freedom.

The pop-up mechanism used to implement the simple rotary actuator is shown in FIGS. 56 and 57. Here, the permanent magnet 116 and magnetic coil 118 are prefabricated components positioned on the pop-up MEMS laminate via pick and place (pick and place II process step 106" in FIG. 34). Once the magnet 116 and coil 118 are secured to the flat pop-up MEMS laminate, the laminate unfolds into a three-dimensional mechanism that positions the magnet 116 inside the coil 118 and allows it to pivot along its axis.

The unfolding process is constrained by two Sarrus linkages 136 that constrain the magnet 116 to rise vertically and the coil 118 to rise and rotate by 90 degrees. After the unfolding process is complete, the unfolding mechanism is locked in place using solder or glue (locking process step 112 in FIG. 34), and the flexures 138 that allow the magnet to pivot inside the coil are released by laser machining (laser machining III process step 46 in FIG. 34). FIGS. 58 and 59 show a simple rotary actuator 140 implemented in pop-up MEMS (unfolded with pick-and-place components attached in FIG. 58 and fully assembled in FIG. 59). The actuator 140 is configured to rotate a 45 degree mirror (also a pick-and-place component) for optical scanning applications.

Note that pop-up MEMS can produce very complex and diverse folding mechanisms; and, therefore, the simple rotary actuator 140 can be implemented in a number of different ways. In the embodiment shown, the coil 118 and magnet 116 rise during unfolding; and the coil 118 slides over the magnet 116. Other embodiments comprise the following: (a) a stationary coil with the folding mechanism positioning the magnet 116 inside the coil 118; (b) a stationary magnet with the folding mechanism positioning the coil 118 around the magnet 116; or (c) other folding mechanisms where both the coil 118 and magnet 116 are moved into the desired position using appropriate mechanical linkages.

As with the VCA designs, a copper-laminated polymer layer can be introduced into the pop-up MEMS laminate and patterned appropriately to be used as a printed circuit board to house drive and control electronics associated with the actuator 140. The board may be populated at the same time that other pick-and-place components, such as the magnet 116 and coil 118, are delivered.

Electronic Components and Integration for Pop-Up MEMS

Pop-up MEMS allow for the fabrication of mechanical and electromechanical devices with dimensions and features in the sub-mm through cm range (e.g., with dimensions in the range from 0.1 mm to 2 cm). One feature of pop-up MEMS is the ability to integrate electronics and discrete electrical components directly into the structure. This section is directed toward how to best accomplish the integration and wiring of electronics in pop-up structures.

Multiple options are available to fabricate and integrate electronics into pop-up devices, including the following: (a) direct fabrication of electrical components into pop-ups and out of pop-up materials (e.g., laser ablating force and strain sensors into a pop-up structure—e.g., by applying a layer of a composition that generates a voltage under stress and shaping it by removing portions with a laser); (b) use of electrical components as mechanical components (e.g., use of flex circuits as hinges) and the use of mechanical components as electrical conduits (e.g., use of structural linkages as electrical vias and connectors); (c) embedding electrical components (e.g., electrodes, LEDs, etc.) into the mechanical structure and mechanical operation of the pop-up mechanism; and (d) the development of electromagnets and wrapped circuits using pop-ups.

The ability to easily incorporate conductive layers is an advantageous feature of the pop-up MEMS process; and special design practices can be followed when routing traces through flexure joints to avoid trace failure. These practices include: selecting a trace thickness and bending radius that does not result in surface strains exceeding the fracture strain of the trace material; ensuring that the trace is as close as possible to the neutral bending axis; and preventing damage to the trace due to compression between inelastic flexure layers.

Hinges in a folding laminate structure can be of a small radius, as shown in FIG. 62, to enable the interconnected parts to pivot approximately about an axis, thereby offering greater precision of movement and positioning. The configuration of FIG. 62 includes two interlocking sections of rigid segments 12 containing and joined by a flexible layer 16 that contains an electrical trace 30 for delivering electrical current to electronic components on the device and/or for communicating electronic signals to and/or from the components to an external processor/controller. As shown, the electrical trace 30 likewise bends about a tight radius, which may strain the electrical trace 30 and potentially hasten the failure of the electrical trace 30.

Minimizing the flexure bending radius is frequently desirable in pop-up MEMS flexures in order for the flexure to approximate a pin joint as closely as possible. In situations where this causes excessive surface strains, however, a hybrid hinge may be employed, as shown in FIG. 63. Such a hinge consists of a mechanical portion with a tight bending radius and an electrical cable portion with a larger bending radius. As shown in FIG. 63, the electrical trace 30 extends between the rigid segments 12 across a cut-out section defined between rigid-segment sections 36 that provides a greater gap between the rigid segments 12 and, therefore, affords the electrical trace 30 a greater radius of curvature than that of the flexible layer 16 at rigid-segment section 34 (shown in the background, beyond the cut-out in FIG. 63). In this embodiment, the electrical trace 30 also includes an outer insulation coating.

In order for the electrical traces 30 to remain close to the neutral bending axis, the traces 30 may be sandwiched between identical layers of flexure material 16, as shown in FIG. 64. However, if the flexure material 16 cannot stretch easily (as is the case with polyimide, a common pop-up MEMS material), extreme bending angles can cause the trace 30 to be compressed and severed by this material 16. To prevent this, gaps may be placed strategically in the flexure material 16 directly over the trace 30 on the outside of the bend. This configuration allows the trace 30 to remain near the neutral bending axis, prevents damage to the trace 30 by the flexure material 16, and maintains a uniform bending radius on the inside of the bend. If the trace 30 must be insulated from the surrounding medium, a sufficiently stretchable insulating layer can cover the newly formed gaps.

Applications in which integrated electronics can be used include the following: (a) sensors or components directly fabricated into pop-up devices (e.g., in the stacking and lamination process) to reduce costs, to remove the need for separate precision alignment, or to allow the design of custom components; (b) articulated mechanisms with electrical power or signals transmitted through conductive pathways in hinges or linkages, which reduces or removes the need for external wiring for pop-up devices; (c) direct fabrication of electromagnetic actuators into pop-up devices (e.g., in the stacking and lamination process); (d) an Ocelli optical sensor made by fabricating a two-dimensional printed circuit board (PCB) with rigid and flexible sections, attaching surface mount components via soldering or reflow, and folding the PCB into a 3D structure; (e) voice coil actuators for pop-ups, where a magnetic coil is fabricated via lamination so that it can be fabricated concurrently with pop-up mechanisms; and (f) a pop-up beam scanner, where a pop-up structure is designed to fold into a simple electromagnetic actuator—here, a separately fabricated coil and magnet are placed on the pop-up structure (e.g., via a pick-and-place process), and the folding process is used to assemble a 3D actuator. In additional embodiments, an LED/phototransistor pair is coupled with an optical interrupter to realize an optical encoder, or a Hall effect sensor is included to track a magnet attached to a moving mechanism, In particular embodiments, the grasper prototypes of FIGS. 17, 22-24, 26, and 29-33 include an integrated strain gauge 72 for force sensing as the grasper is performing a manipulation task. The strain gauge 72 can be included, along with an electrically conductive layer that includes conductive circuit traces that are electrically coupled with the strain gauge, in at least one of the pivoting sub-modules that form the grasper, wherein each sub-module includes a jaw. In additional embodiments, the custom strain gauge 72 of FIG. 19 is directly manufactured into the pop-up structure. In additional embodiments, flex-circuits are used as the compliant flexure hinge layer, as shown in FIGS. 62 and 63, to allow for internal wiring for electrical components—in this case, surface mount electronics. In the embodiments of FIGS. 45-53, an electromagnetic coil formed from two patterned and laminated flex circuits create an actuator for pop-up devices. Further still, the Ocelli optical sensor shown in FIGS. 60 and 6*a* are composed of rigid and flexible circuits 96 and components 97 on a substrate and folded along fold lines 98 into three-dimensional structure. Finally, in the embodiments of FIGS. 58 and 59, a pop-up MEMS beam scanner is composed of a hybrid of a conventional electromagnetic coil and a pop-up 3D assembly structure.

The integration of electronics (e.g., sensors and actuators) directly or in parallel into the manufacturing of pop-up structures allows for fabrication of customized sensors and actuators based on functional requirements with negligible additional manufacturing overhead. Additionally, one can integrate sensing, on-board actuation, and other commercial off-the-shelf electronic components into the pop-up structure without additional wiring, separate assembly, or manufacturing steps.

In describing embodiments of the invention, specific terminology is used for the sake of clarity. For the purpose of description, specific terms are intended to at least include technical and functional equivalents that operate in a similar manner to accomplish a similar result. Additionally, in some instances where a particular embodiment of the invention includes a plurality of system elements or method steps, those elements or steps may be replaced with a single element or step; likewise, a single element or step may be replaced with a plurality of elements or steps that serve the same purpose. Further, where parameters for various properties or other values are specified herein for embodiments of the invention, those parameters or values can be adjusted up or down by $1/100^{th}$, $1/50^{th}$, $1/20^{th}$, $1/10^{th}$, $1/5^{th}$, $1/3^{rd}$, $1/2$, $2/3^{rd}$, $3/4^{th}$, $4/5^{th}$, $9/10^{th}$, $19/20^{th}$, $49/50^{th}$, $99/100^{th}$, etc. (or up by a factor of 1, 2, 3, 4, 5, 6, 8, 10, 20, 50, 100, etc.), or by rounded-off approximations thereof, unless otherwise specified. Moreover, while this invention has been shown and described with references to particular embodiments thereof, those skilled in the art will understand that various substitutions and alterations in form and details may be made therein without departing from the scope of the invention. Further still, other aspects, functions and advantages are also within the scope of the invention; and all embodiments of the invention need not necessarily achieve all of the advantages or possess all of the characteristics described above. Additionally, steps, elements and features discussed herein in connection with one embodiment can likewise be used in conjunction with other embodiments. The contents of references, including reference texts, journal articles, patents, patent applications, etc., cited throughout the text are hereby incorporated by reference in their entirety; and appropriate components, steps, and characterizations from these references may or may not be included in embodiments of this invention. Still further, the components and steps identified in the Background section are integral to this disclosure and can be used in conjunction with or substituted for components and steps described elsewhere in the disclosure within the scope of the invention. In method claims, where stages are recited in a particular order—with or without sequenced prefacing characters added for ease of reference—the stages are not to be interpreted as being temporally limited to the order in which they are recited unless otherwise specified or implied by the terms and phrasing.

What is claimed is:

1. A laminate device for manipulating or altering structures, the device comprising:
   a laminate stack comprising two sub-modules, each comprising at least one rigid substrate laminated to a less-rigid flexible layer, wherein each sub-module includes a body and a jaw extending from the body, and wherein the sub-modules are joined at the body and biased so that the jaws are in contact (closed) or spread apart (open); and
   an actuation device, wherein the actuation device includes at least one actuator selected from a shape memory alloy actuator and a piezoelectric actuator, wherein the actuator is coupled with at least one of the jaws and configured to overcome the bias and actuate the jaw(s) to open or close the jaws when displaced.

2. The laminate device of claim 1, wherein the jaws include end effectors configured to grasp or join structures.

3. The laminate device of claim 1, wherein the jaws include blades for cutting structures.

4. The laminate device of claim 1, wherein the jaws are configured to separate by a maximum of 0.1 to 10 mm when opened.

5. The laminate device of claim 1, further comprising an electrically conductive layer including electrical wiring in at least one of the sub-modules.

6. The laminate device of claim 5, further comprising a strain gauge mounted on or in at least one of the jaws, electrically coupled with the electrical wiring, and configured to detect force acting on the jaw.

7. The laminate device of claim 5, further comprising at least one electrode in at least one of the jaws for electro-cauterization or ablation, wherein the electrode is electrically coupled with the electrical wiring.

8. The laminate device of claim 1, wherein each sub-module of the laminate stack includes at least the following five sub-layers: a flexible layer, adhesive layers on both sides of the flexible layer, and two rigid structural layers bonded to the adhesive layers.

9. The laminate device of claim 1, further comprising a restoring element that biases the submodules to force the jaws in contact with one another or to force the jaws apart from one another when unactuated.

10. A method for micro-surgery, comprising:
    percutaneously inserting the laminate device of claim 1 into an organism; and
    a) grasping, cutting or connecting at least one internal organ, tissue, or vessel in the organism with the jaws of the laminate device; or
    b) manipulating another surgical tube inside the organism with the laminate device.

11. The method of claim 10, further comprising actuating the jaws inside the body by at least one of the following:
    altering the shape of the shape memory alloy actuator coupled with at least one of the jaws; and
    applying a voltage to the piezoelectric actuator coupled with at least one of the jaws.

12. The method of claim 11, further comprising detecting interaction with the organ, tissue or organism by detecting a change in resistance of a strain gauge mounted on or in at least one of the jaws.

* * * * *